(12) United States Patent
Jiang et al.

(10) Patent No.: US 9,738,780 B2
(45) Date of Patent: Aug. 22, 2017

(54) CROSSLINKED MIXED CHARGE HYDROGELS

(71) Applicant: University of Washington through its Center for Commercialization, Seattle, WA (US)

(72) Inventors: Shaoyi Jiang, Redmond, WA (US); Hong Xue, Pleasanton, CA (US); Wei Yang, Seattle, WA (US); Louisa R. Carr, Schenectady, NY (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

(21) Appl. No.: 15/211,278

(22) Filed: Jul. 15, 2016

(65) Prior Publication Data

US 2017/0009069 A1 Jan. 12, 2017

Related U.S. Application Data

(60) Division of application No. 14/457,801, filed on Aug. 12, 2014, now Pat. No. 9,394,435, which is a division of application No. 13/463,648, filed on May 3, 2012, now Pat. No. 8,835,671, which is a continuation of application No. PCT/US2010/055875, filed on Nov. 8, 2010.

(60) Provisional application No. 61/259,074, filed on Nov. 6, 2009.

(51) Int. Cl.
| | |
|---|---|
| *C08L 33/14* | (2006.01) |
| *A61K 41/00* | (2006.01) |
| *A61L 27/34* | (2006.01) |
| *A61L 27/52* | (2006.01) |
| *A61L 31/10* | (2006.01) |
| *C07C 229/12* | (2006.01) |
| *A61L 29/08* | (2006.01) |
| *A61L 29/14* | (2006.01) |
| *A61L 31/14* | (2006.01) |
| *C08F 26/02* | (2006.01) |
| *C08L 33/10* | (2006.01) |
| *C08J 3/075* | (2006.01) |
| *C12Q 1/54* | (2006.01) |

(52) U.S. Cl.
CPC .......... *C08L 33/14* (2013.01); *A61K 41/0019* (2013.01); *A61L 27/34* (2013.01); *A61L 27/52* (2013.01); *A61L 29/085* (2013.01); *A61L 29/145* (2013.01); *A61L 31/10* (2013.01); *A61L 31/145* (2013.01); *C07C 229/12* (2013.01); *C08F 26/02* (2013.01); *C08J 3/075* (2013.01); *C08L 33/10* (2013.01); *C12Q 1/54* (2013.01); *C12Y 101/03004* (2013.01); *C08J 2433/14* (2013.01); *C08L 2201/54* (2013.01); *C08L 2312/00* (2013.01); *G01N 2333/904* (2013.01); *Y10T 428/31786* (2015.04)

(58) Field of Classification Search
CPC ........ A61L 27/34; A61L 27/52; A61L 29/085; A61L 29/145; A61L 31/10; A61L 31/145; A61K 41/0019; C07C 229/12; C08F 26/02; C08L 33/10; C08L 2201/54; C08L 2312/00; C08J 3/075; C08J 2433/14
USPC ........................................................ 524/403
See application file for complete search history.

(56) References Cited

U.S. PATENT DOCUMENTS

| | | | | |
|---|---|---|---|---|
| 2007/0104654 | A1* | 5/2007 | Hsieh | A61K 9/1075 424/46 |
| 2009/0197791 | A1* | 8/2009 | Balastre | A61K 8/8158 510/407 |

FOREIGN PATENT DOCUMENTS

| | | |
|---|---|---|
| JP | 2005-179155 A | 7/2005 |
| JP | 2007130194 A | 5/2007 |
| WO | 2007/024393 A2 | 3/2007 |
| WO | 2008/019381 A1 | 2/2008 |
| WO | 2008/083390 A2 | 7/2008 |
| WO | 2009/067562 A1 | 5/2009 |

OTHER PUBLICATIONS

Berger, J., et al., "Structure and Interactions in Covalently and Ionically Crosslinked Chitosan Hydrogels for Biomedical Applications," European Journal of Pharmaceutics and Biopharmaceutics 57(1):19-34, Jan. 2004.

Carr, L.R., et al., "Functionalizable and Nonfouling Zwitterionic Carboxybetaine Hydrogels With a Carboxybetaine Dimethacrylate Crosslinker," Biomaterials 32(4):961-968, Feb. 2011.

Chang, Y., et al., "Development of Biocompatible Interpenetrating Polymer Networks Containing a Sulfobetaine-Based Polymer and a Segmented Polyurethane for Protein Resistance," Biomacromolecules 8(1):122-127, Jan. 2007.

Chang, Y., et al., "Highly Protein-Resistant Coatings From Well-Defined Diblock Copolymers Containing Sulfobetaines," Langmuir 22(5):2222-2226, Feb. 2006.

Cheng, G., et al., "Zwitterionic Carboxybetaine Polymer Surfaces and Their Resistance to Long-Term Biofilm Formation," Biomaterials 30(28):5234-5240, Oct. 2009.

(Continued)

*Primary Examiner* — Michael M Bernshteyn
(74) *Attorney, Agent, or Firm* — Christensen O'Connor Johnson Kindness PLLC

(57) ABSTRACT

Zwitterionic crosslinking agents, crosslinked zwitterionic hydrogels prepared from copolymerization of zwitterionic monomers with the zwitterionic crosslinking agent, methods for making crosslinked zwitterionic hydrogels, and devices that include and methods that use the crosslinked zwitterionic hydrogels.

25 Claims, 23 Drawing Sheets

(56) References Cited

OTHER PUBLICATIONS

Corkhill, P.H., et al., "Synthetic Hydrogels. VI. Hydrogel Composites as Wound Dressings and Implant Materials," Biomaterials 10(1):3-10, Jan. 1989.
Couvreur, P., and C. Vauthier, "Nanotechnology: Intelligent Design to Treat Complex Disease," Pharmaceutical Research 23(7):1417-1450, Jul. 2006.
Galeska, I., et al., "Characterization and Biocompatibility Studies of Novel Humic Acids Based Films as Membrane Material for an Implantable Glucose Sensor," Biomacromolecules 2(4):1249-1255, Winter 2001.
Goda, T., et al., "Protein Adsorption Resistance and Oxygen Permeability of Chemically Crosslinked Phospholipid Polymer Hydrogel for Ophthalmologic Biomaterials," Journal of Biomedical Materials Research Part B: Applied Biomaterials 89(1):184-190, Apr. 2009.
Goda, T., et al., "Water Structure and Improved Mechanical Properties of Phospholipid Polymer Hydrogel With Phosphorylcholine Centered Intermolecular Cross-Linker," Polymer 47(4):1390-1396, Feb. 2006.
Gref, R., et al., "'Stealth' Corona-Core Nanoparticles Surface Modified by Polyethylene Glycol (PEG): Influences of the Corona (PEG Chain Length and Surface Density) and of the Core Composition on Phagocytic Uptake and Plasma Protein Adsorption," Colloids and Surfaces B: Biointerfaces 18(3-4):301-313, Oct. 2000.
International Search Report and Written Opinion mailed Jul. 28, 2011, issued in corresponding International Application No. PCT/US2010/055875, filed Nov. 8, 2010,7 pages.
International Preliminary Report on Patentability and Written Opinion mailed May 8, 2012, issued in corresponding International Application No. PCT/US2010/055875, filed Nov. 8,2010, 5 pages.
Ladd, J., et al., "Zwitterionic Polymers Exhibiting High Resistance to Nonspecific Protein Adsorption From Human Serum and Plasma," Biomacromolecules 9(5):1357-1361, May 2008.
Langer, R., and J.P. Vacanti, "Tissue Engineering," Science 260(5110):920-926, May 1993.
Lin, C.-C., and A.T. Metters, "Hydrogels in Controlled Release Formulations: Network Design and Mathematical Modeling," Advanced Drug Delivery Reviews 58(12-13):1379-1408, Nov. 2006.
Matsuura, K., et al., "Carboxybetaine Polymer-Protected Gold Nanoparticles: High Dispersion Stability and Resistance Against Non-Specific Adsorption of Proteins," Macromolecular Chemistry and Physics 208(8):862-873, Apr. 2007.
Moghimi, S.M., et al., "Nanomedicine: Current Status and Future Prospects," FASEB Journal 19(3):311-330, Mar. 2005.

Nayak, S., et al., "Folate-Mediated Cell Targeting and Cytotoxicity Using Thermoresponsive Microgels," Journal of the American Chemical Society 126(33):10258-10259, Aug. 2004.
Notification of the First Office Action received Jul. 22, 2013, issued in corresponding Chinese Application No. 201080055967.X, filed Nov. 8, 2010, 23 pages.
Ogawara, K.-I., et al., "A Novel Strategy to Modify Adenovirus Tropism and Enhance Transgene Delivery to Activated Vascular Endothelial Cells In Vitro and In Vivo," Human Gene Therapy 15(5):433-443, May 2004.
Deppas, N.A., et al., "Hydrogels in Biology and Medicine: From Molecular Principles to Bionanotechnology," Advanced Materials 18(11):1345-1360, Jun. 2006.
Peppas, N.A., et al., "Hydrogels in Pharmaceutical Formulations," European Journal of Pharmaceutics and Biopharmaceutics 50(1):27-46, Jul. 2000.
Raemdonck, K., et al., "Advanced Nanogel Engineering for Drug Delivery," Soft Matter 5(4):707-715, Dec. 2008.
Shi, L., et al., "Poly(N-vinylformamide) Nanogels Capable of pH-Sensitive Protein Release," Macromolecules 41 (17):6546-6554, Sep. 2008.
Tominey, A., et al., "Supramolecular Binding of Protonated Amines to a Receptor Microgel in Aqueous Medium," Chemical Communications (23):2492-2494, Jun. 2006.
Tsai, W.B., et al., "Human Plasma Fibrinogen Adsorption and Platelet Adhesion to Polystyrene," Journal of Biomedical Materials Research 44(2):130-139, Feb. 1999.
Vinogradov, S., et al., "Poly(ethylene glycol)-Polyethyleneimine NanoGel™ Particles: Novel Drug Delivery Systems for Antisense Oligonucleotides," Colloids and Surfaces B: Biointerfaces 16(1-4):291-304, Nov. 1999.
Yang, W., et al., "Pursuing 'Zero' Protein Adsorption of Poly(carboxybetaine) From Undiluted Blood Serum and Plasma," Langmuir 25(19):11911-11916, Oct. 2009.
Yu, B., et al., "Use of Hydrogel Coating to Improve the Performance of Implanted Glucose Sensors," Biosensors and Bioelectronics 23(8):1278-1284, Mar. 2008.
Zhang, Z., et al., "Dual-Functional Biomimetic Materials: Nonfouling Poly(carboxybetaine) With Active Functional Groups for Protein Immobilization," Biomacromolecules 7(12):3311-3315, Dec. 2006.
Zhang, Z., et al., "Superlow Fouling Sulfobetaine and Carboxybetaine Polymers on Glass Slides," Langmuir 22(24):10072-10077, Nov. 2006.
Zhang, Z., et al., "Surface Grafted Sulfobetaine Polymers via Atom Transfer Radical Polymerization as Superlow Fouling Coatings," Journal of Physical Chemistry B 110(22):10799-10804, Jun. 2006.

* cited by examiner

CROSSLINKED MIXED CHARGE HYDROGELS

CROSS-REFERENCES TO RELATED APPLICATIONS

This application is a division of U.S. patent application Ser. No. 14/457,801, filed Aug. 12, 2014, now U.S. Pat. No. 9,394,435, which is a division of U.S. patent application Ser. No. 13/463,648, filed May 3, 2012, now U.S. Pat. No. 8,835,671, which is a continuation of International Application No. PCT/US2010/055875, filed Nov. 8, 2010, which claims the benefit of U.S. Patent Application No. 61/259,074, filed Nov. 6, 2009, each of which is expressly incorporated herein by reference in its entirety.

STATEMENT OF GOVERNMENT LICENSE RIGHTS

This invention was made with Government support under Contract Nos. N000140910137 and N000140711036 awarded by the Office of Naval Research. The Government has certain rights in the invention.

BACKGROUND

Hydrogels have long been of interest for biological and biomaterial applications due to their high water content that mimics the interstitial tissue environment, ensures high diffusive permeability, and provides biomimetic mechanical strengths. Particular interest has been given to PEG hydrogels and poly(2-hydroxyethyl methacrylate) (pHEMA) hydrogels because, in addition to the general properties of hydrogels, they are also commonly considered be low fouling, bioinert, and versatile.

pHEMA hydrogels have found use in and been studied for applications such as contact lenses, artificial cornea, drug delivery vehicles, cartilage substitutes, and tissue scaffolds, among others. The hydration of pHEMA, however, is lower than that of native tissue, and its fouling, while low, is higher than other nonfouling materials. Furthermore, pHEMA functionalization via the hydroxyl group is generally difficult.

PEG hydrogels are routinely used, and can only be modified for applications that require a bioinert background with specific added bioactive functionalities for controlled in vitro and in vivo uses when additional functional groups are introduced into PEG hydrogels. However, it has been found that PEG is subject to oxidation. The susceptibility of PEG to oxidative damage reduces its utility for applications that require long-term material stability. For applications in which maximal biological stability and nonfouling are required, however, PEG-based materials are insufficient.

Recently, zwitterionic compounds, including poly(carboxybetaine methacrylate) (pCBMA, Scheme 1, structure 1), have been demonstrated to be ultra-low-fouling, meaning that surfaces coated with these polymers allow less than 5 ng/cm$^2$ protein adsorption. It was also demonstrated that surfaces coated with zwitterionic poly(carboxybetaine methacrylate) greatly resist non-specific protein adsorption, even from undiluted blood plasma and serum and also prohibit long-term bacterial colonization by *Pseudomonas aeruginosa* for up to 10 days at room temperature. The ultra-low-fouling of zwitterionic materials is due to high hydration around the opposing charges and the high energetics required to remove that hydration layer. Furthermore, CBMA (carboxybetaine methacrylate) is functionalizable through conventional EDC/NHS chemistry.

Because of the high hydration and ultralow fouling properties of zwitterionic materials, zwitterionic hydrogels are of interest as hydrogels with superior suitability for biomedical applications. Low protein adhesion on sulfobetaine methacrylate (SBMA) and mixed charge hydrogels, and low cell adhesion on carboxybetaine methacrylate gels, have been demonstrated. The zwitterionic hydrogels studied so far, however, have shown low mechanical strength, which limits their potential biological uses. A need therefore exists for hydrogels having improved mechanical properties.

Another fundamentally limiting feature of these zwitterionic hydrogels is the dearth of hydrophilic crosslinkers. The most commonly used of the commercially available "hydrophilic" crosslinker is N,N'-methylenebis(acrylamide) (MBAA, Scheme 1, structure 2). Water-soluble at very low concentrations, this crosslinker is only moderately soluble at crosslinker concentrations around 10%, especially in the salt solutions that are ideal for zwitterionic hydrogel formation. Additionally problematic for polymerization with pSBMA and pCBMA is the inherent incompatibility of the polymerizable moieties: the greatly different chemical structure of the crosslinker may result in poor incorporation into the growing methacrylate polymer chains. Perhaps the most unacceptable feature of MBAA as a crosslinker in zwitterionic hydrogels is that it does not structure water the way the zwitterionic monomers do. Structured water around the opposing charges in a zwitterionic material provides the nonfouling mechanism; MBAA will disrupt the ordered water and present locations where proteins, bacteria, and even cells, may bind and foul the hydrogel. Furthermore, the MBAA crosslinker is not functionalizable.

A need exists for crosslinked zwitterionic hydrogels that retain the advantageous properties of non-crosslinked zwitterionic hydrogels. The present invention seeks to fulfill this need and provides further related advantages.

SUMMARY OF THE INVENTION

The present invention provides a zwitterionic crosslinking agent, crosslinked zwitterionic hydrogels prepared from copolymerization of zwitterionic monomers with the zwitterionic crosslinking agent, methods for making crosslinked zwitterionic hydrogels, and devices that include and methods that use the crosslinked zwitterionic hydrogels.

In one aspect, the invention provides, a crosslinker having the formula:

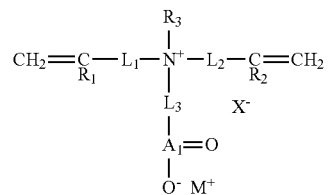

wherein $R_1$ and $R_2$ are independently selected from the group consisting of hydrogen, fluorine, trifluoromethyl, C1-C6 alkyl, and C6-C12 aryl groups;

$R_3$ is selected from the group consisting of C1-C6 alkyl, C6-C12 aryl, $CH_2=C(R_1)-L_1-$, and $CH_2=C(R_2)-L_2-$;

$L_1$ and $L_2$ are independently selected from the group consisting of $-C(=O)O-(CH_2)_n-$ and $-C(=O)NH-(CH_2)_n-$, wherein n is an integer from 1 to 20;

$L_3$ is $-(CH_2)_n-$, where n is an integer from 1 to 20;

$A_1$ is C, S, SO, P, or PO;

$X^-$ is the counter ion associated with the $N^+$ cationic center; and $M^+$ is a counterion associated with the $(A_1=O)O^-$ anionic center.

In one embodiment, $A_1$ is C or SO.

In another aspect, the invention provides a crosslinked hydrogel that is crosslinked with the crosslinker of the invention. In one embodiment, the crosslinked hydrogel comprises a crosslinked polymer having repeating units and a plurality of crosslinks, wherein each repeating unit has the formula:

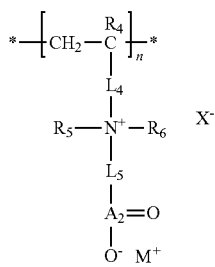

wherein $R_4$ is selected from the group consisting of hydrogen, fluorine, trifluoromethyl, C1-C6 alkyl, and C6-C12 aryl groups;

$R_5$ and $R_6$ are independently selected from the group consisting of alkyl and aryl, or taken together with the nitrogen to which they are attached form a cationic center;

$L_4$ is a linker that covalently couples the cationic center $[N^+(R_5)(R_6)]$ to the polymer backbone $[—(CH_2—CR_4)_n—]$;

$L_5$ is a linker that covalently couples the anionic center $[A_2(=O)—O^-]$ to the cationic center;

$A_2$ is C, S, SO, P, or PO;

$M^+$ is a counterion associated with the $(A_2=O)O^-$ anionic center;

$X^-$ is a counter ion associated with the cationic center;

n is an integer from 5 to about 10,000; and wherein each crosslink has the formula:

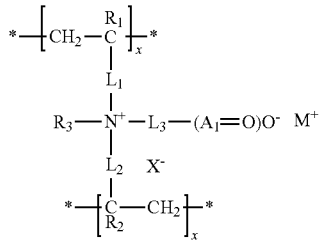

wherein $R_1$ and $R_2$ are independently selected from the group consisting of hydrogen, fluorine, trifluoromethyl, C1-C6 alkyl, and C6-C12 aryl groups;

$R_3$ is selected from the group consisting of C1-C6 alkyl, C6-C12 aryl, $CH_2=C(R_1)-L_1-$, $CH_2=C(R_2)-L_2-$, or $R_3$ is the residual portion of a third crosslink, $-L_1-CR_1—CH_2—$ or $-L_2-CR_2—CH_2—)$;

$L_1$ and $L_2$ are independently selected from the group consisting of $—C(=O)O—(CH_2)_n—$ and $—C(=O)NH—(CH_2)_n—$, wherein n is an integer from 1 to 20;

$L_3$ is $—(CH_2)_n—$, where n is an integer from 1 to 20;

$A_1$ is C, S, SO, P, or PO;

x is an integer from about 5 to about 10,000;

$X^-$ is the counter ion associated with the $N^+$ cationic center; and $M^+$ is a counterion associated with the $(A=O)O^-$ anionic center.

In another embodiment, the crosslinked hydrogel comprises a crosslinked polymer having repeating, wherein each repeating unit has the formula:

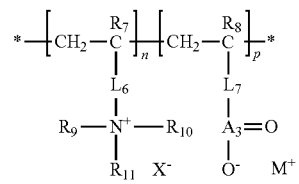

wherein $R_7$ and $R_8$ are independently selected from hydrogen, fluorine, trifluoromethyl, C1-C6 alkyl, and C6-C12 aryl groups;

$R_9$, $R_{10}$, and $R_{11}$ are independently selected from alkyl and aryl, or taken together with the nitrogen to which they are attached form a cationic center;

$A_3(=O)—OM)$ is an anionic center, wherein $A_3$ is C, S, SO, P, or PO, and M is a metal or organic counterion;

$L_6$ is a linker that covalently couples the cationic center $[N^+(R_9)(R_{10})(R_{11})]$ to the polymer backbone;

$L_7$ is a linker that covalently couples the anionic center $[A(=O)—OM]$ to the polymer backbone;

$X^-$ is the counter ion associated with the cationic center;

n is an integer from 5 to about 10,000; and p is an integer from 5 to about 10,000.

In another aspect, the invention provides a surface of a substrate, wherein the surface comprises crosslinked hydrogel of the invention.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

The present invention provides a zwitterionic crosslinking agent, crosslinked zwitterionic hydrogels prepared from copolymerization of zwitterionic monomers with the zwitterionic crosslinking agent, methods for making crosslinked zwitterionic hydrogels, and devices that include and methods that use the crosslinked zwitterionic hydrogels.

Zwitterionic Crosslinking Agent

In one aspect, the invention provides a zwitterionic crosslinking agent. The zwitterionic crosslinking agent can be copolymerized with suitable polymerizable monomers and comonomers to provide crosslinked polymers and crosslinked copolymers.

The zwitterionic crosslinking agent is advantageously used to prepare crosslinked polymers and crosslinked copolymers, such as crosslinked hydrogels, by copolymerization with one or more zwitterionic monomers, or by copolymerization with one or more charged comonomers, such as ion pair comonomers.

The zwitterionic crosslinking agent of the invention has formula (I):

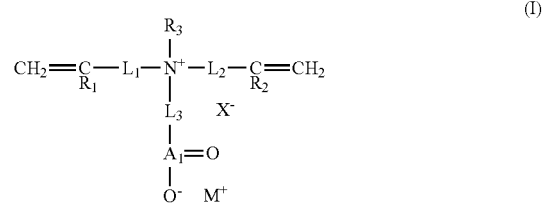

wherein $R_1$ and $R_2$ are independently selected from hydrogen, fluorine, trifluoromethyl, C1-C6 alkyl, and C6-C12 aryl groups;

$R_3$ is selected from C1-C6 alkyl, C6-C12 aryl, $CH_2=C(R_1)-L_1-$, or $CH_2=C(R_2)-L_2-$;

$L_1$ and $L_2$ are independently selected from the group consisting of $-C(=O)O-(CH_2)_n-$ and $-C(=O)NH-(CH_2)_n-$, wherein n is an integer from 1 to 20;

$L_3$ is —$(CH_2)_n$—, where n is an integer from 1 to 20; and
$A_1$ is C, S, SO, P, or PO;
$X^-$ is the counter ion associated with the $N^+$ cationic center; and
$M^+$ is a metal or organic counterion associated with the (A=O)$O^-$ anionic center.

In one embodiment, $R_1$, $R_2$, and $R_3$ are C1-C3 alkyl. In one embodiment, $R_1$, $R_2$, and $R_3$ are methyl.

In one embodiment, $L_1$ and $L_2$ are —C(=O)O—$(CH_2)_n$—, wherein n is 1-6. In one embodiment, $L_1$ and $L_2$ are —C(=O)O—$(CH_2)_2$—.

In one embodiment, $L_3$ is —$(CH_2)_n$—, wherein n is 1-6. In one embodiment, $L_3$ is —$(CH_2)$—.

In one embodiment, $A_1$ is C. In one embodiment, $A_1$ is SO.

Figure 1:
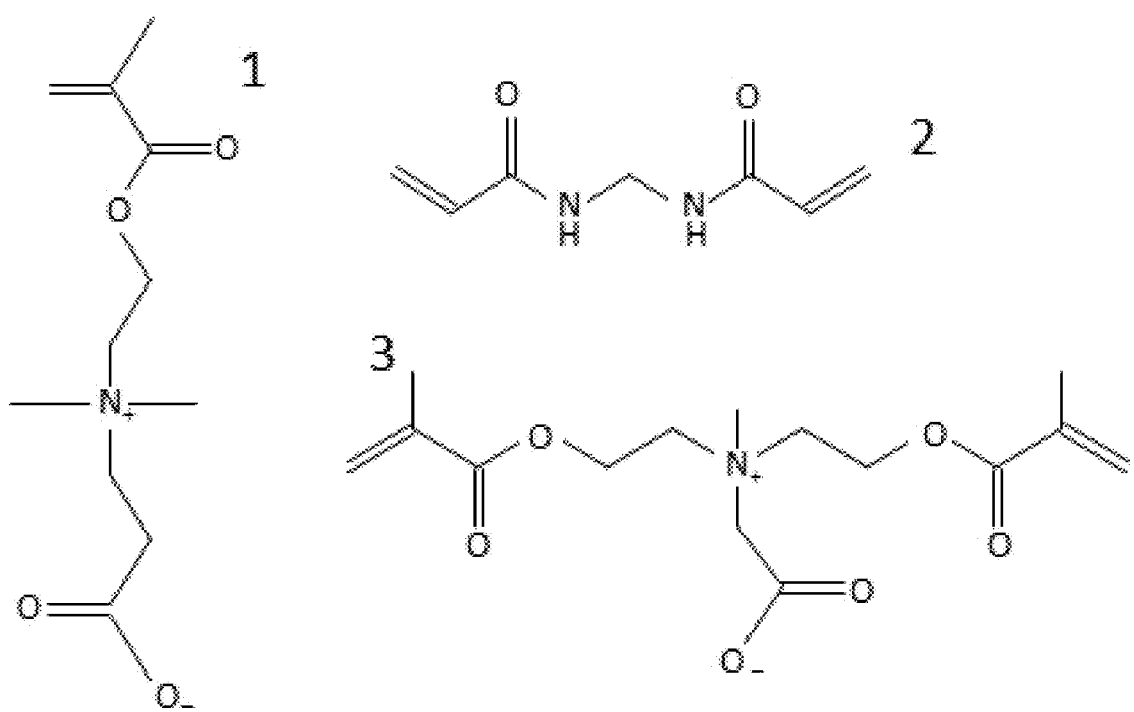
FIG. 1 illustrates the chemical structures of a carboxybetaine monomer, carboxybetaine methacrylate (CBMA) (1), N,N'-methylenebis(acrylamide) (MBAA) (2), and carboxybetaine dimethacrylate (CBMAX) (3).

FIG. 1 illustrates the chemical structure of a representative zwitterionic cros slinking agent of the invention, see Compound 3, referred to herein as CBMAX. The preparation of a representative zwitterionic crosslinking agent of the invention, CBMAX, is described in Example 1 and illustrated schematically in FIG. 2.

Crosslinked Zwitterionic Hydrogels

In another aspect, the invention provides crosslinked zwitterionic hydrogels prepared from copolymerization of zwitterionic monomers with the zwitterionic crosslinking agent. The zwitterionic crosslinking agent can be copolymerized with suitable polymerizable monomers and comonomers to provide crosslinked polymers and cros slinked copolymers.

The crosslinked hydrogels of the invention are crosslinked polymers having repeating groups and crosslinks derived from the zwitterionic crosslinking agent.

Zwitterionic Monomers.

In one embodiment, the crosslinked hydrogels of the invention are crosslinked polymers prepared from copolymerization of the zwitterionic crosslinking agent and suitable polymerizable zwitterionic monomers. In this embodiment, the crosslinked polymer (e.g., hydrogel) has repeating units having formula (II):

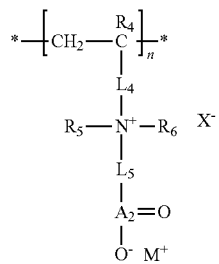

wherein $R_4$ is selected from hydrogen, fluorine, trifluoromethyl, C1-C6 alkyl, and C6-C12 aryl groups;

$R_5$ and $R_6$ are independently selected from alkyl and aryl, or taken together with the nitrogen to which they are attached form a cationic center;

$L_4$ is a linker that covalently couples the cationic center [$N^+(R_5)(R_6)$] to the polymer backbone [—$(CH_2-CR_4)_n$—];

$L_5$ is a linker that covalently couples the anionic center [$A_2$(=O)$O^-$] to cationic center;

$A_2$ is C, S, SO, P, or PO;

$M^+$ is a metal or organic counterion associated with the ($A_2$=O)$O^-$ anionic center;

$X^-$ is the counter ion associated with the cationic center;
n is an integer from 5 to about 10,000; and
* represents the point at which the repeating unit is covalently linked to either an adjacent repeating unit or the zwitterionic crosslink.

In one embodiment, $R_4$ is C1-C3 alkyl.

$R_5$ and $R_6$ are independently selected from alkyl and aryl, or taken together with the nitrogen to which they are attached form a cationic center. In one embodiment, $R_5$ and $R_6$ are C1-C3 alkyl.

In certain embodiments, $L_4$ is selected from the group consisting of —C(=O)O—$(CH_2)_n$— and —C(=O)NH—$(CH_2)_n$—, wherein n is an integer from 1 to 20. In certain embodiments, $L_4$ is —C(=O)O—$(CH_2)_n$—, wherein n is 1-6.

In certain embodiments, $L_5$ is —$(CH_2)_n$—, where n is an integer from 1 to 20.

In certain embodiments, $A_2$ is C or SO.

In certain embodiments, n is an integer from 5 to about 5,000.

In one embodiment, $R_4$, $R_5$, and $R_6$ are methyl, $L_4$ is —C(=O)O—$(CH_2)_2$—, $L_5$ is —$(CH_2)$—, $A_1$ is C, and n is an integer from 10 to about 1,000.

In addition to the crosslinked polymer (e.g., hydrogel) having repeating units having formula (II) above, the crosslinked polymer includes zwitterionic crosslinks having formula (III):

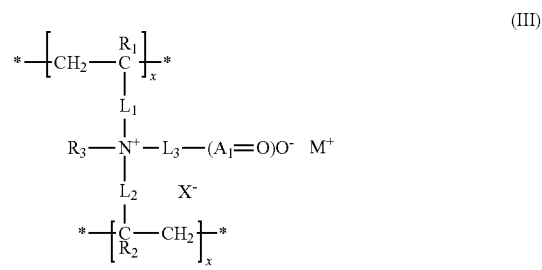

wherein $R_1$, $R_2$, $R_3$, $L_1$, $L_2$, $L_3$, $A_1$, $X^-$, and $M^+$ are as described above for the zwitterionic crosslinking agent (formula (I), and x is an integer from about 5 to about 10,000. For the crosslinked hydrogel where $R_3$ includes a polymerizable group, the hydrogel is further crosslinked through $R_3$, as shown above (-$L_1$-$CR_1$—$CH_2$— and -$L_2$-$CR_2$—$CH_2$—).

The crosslinked zwitterionic hydrogels of the invention can be prepared by copolymerization of the zwitterionic crosslinking agent with monomers having formula (IV):

$$CH_2=C(R_4)-L_4-N^+(R_5)(R_6)-L_5-A_2(=O)O^-M^+X^- \qquad (IV)$$

wherein $R_4$, $R_5$, $R_6$, $L_4$, $L_5$, $A_2$, $X^-$, and $M^+$ are as described above for the repeating unit of formula (II).

Representative crosslinked zwitterionic polymers of the invention have formula (V):

$$PB-(L_4-N^+(R_5)(R_6)-L_5-A_2(=O)O^-M^+)_n(X^-)_n \qquad (V)$$

wherein $R_5$, $R_6$, $L_4$, $L_5$, $A_2$, $X^-$, $M^+$, and n are as described above for the repeating unit of formula (II), and PB is the polymer backbone that includes repeating units [formula (II)] and crosslinks [formula (III)].

The preparation and characteristics of a representative crosslinked zwitterionic hydrogel of the invention, CBMA/CBMAX, is described in Example 2.

Crosslinked Mixed Charge Hydrogels

In another aspect, the invention provides crosslinked mixed charge copolymers (or hydrogels) prepared from copolymerization of ion pair comonomers with the zwitterionic crosslinking agent.

As used herein, the term "mixed charge copolymer (or hydrogel)" refers to a copolymer having a polymer backbone, a plurality of positively charged repeating units, and a plurality of negatively charged repeating units. In the practice of the invention, these copolymers may be prepared by polymerization of an ion-pair comonomer.

The mixed charge copolymer includes a plurality of positively charged repeating units, and a plurality of negatively charged repeating units. In one embodiment, the mixed charge copolymer is substantially electronically neutral. As used herein, the term "substantially electronically neutral" refers to a copolymer that imparts advantageous nonfouling properties to the copolymer. In one embodiment, a substantially electronically neutral copolymer is a copolymer having a net charge of substantially zero (i.e., a copolymer about the same number of positively charged repeating units and negatively charged repeating units). In one embodiment, the ratio of the number of positively charged repeating units to the number of the negatively charged repeating units is from about 1:1.1 to about 1:0.5. In one embodiment, the ratio of the number of positively charged repeating units to the number of the negatively charged repeating units is from about 1:1.1 to about 1:0.7. In one embodiment, the ratio of the number of positively charged repeating units to the number of the negatively charged repeating units is from about 1:1.1 to about 1:0.9.

Ion Pair Comonomers.

In one embodiment, the crosslinked hydrogels of the invention are crosslinked polymers prepared from copolymerization of the zwitterionic crosslinking agent and suitable polymerizable ion pair comonomers.

Representative ion-pair comonomers useful in the invention have formulas (VI) and (VII):

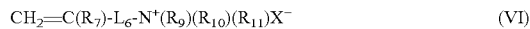
(VI)

(VII)

In this embodiment, the crosslinked polymer (e.g., hydrogel) has repeating units having formula (VIII):

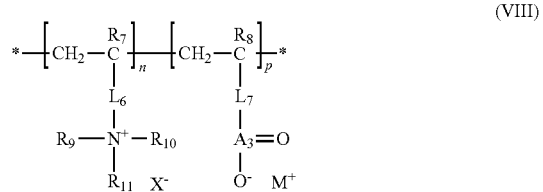
(VIII)

wherein $R_7$ and $R_8$ are independently selected from hydrogen, fluorine, trifluoromethyl, C1-C6 alkyl, and C6-C12 aryl groups;

$R_9$, $R_{10}$, and $R_{11}$ are independently selected from alkyl and aryl, or taken together with the nitrogen to which they are attached form a cationic center;

$A_3(=O)$—OM) is an anionic center, wherein $A_3$ is C, S, SO, P, or PO, and M is a metal or organic counterion;

$L_6$ is a linker that covalently couples the cationic center $[N^+(R_9)(R_{10})(R_{11})]$ to the polymer backbone;

$L_7$ is a linker that covalently couples the anionic center $[A(=O)$—OM] to the polymer backbone;

$X^-$ is the counter ion associated with the cationic center;

n is an integer from 5 to about 10,000;

p is an integer from 5 to about 10,000; and

* represents the point at which the repeating units is covalently linked to either and adjacent repeating unit or the zwitterionic crosslink.

In one embodiment, $R_7$ and $R_8$ are C1-C3 alkyl.

$R_9$, $R_{10}$, and $R_{11}$ are independently selected from alkyl and aryl, or taken together with the nitrogen to which they are attached form a cationic center. In one embodiment, $R_9$, $R_{10}$, and $R_{11}$ are C1-C3 alkyl.

In certain embodiments, $L_6$ is selected from the group consisting of —C(=O)O—(CH$_2$)$_n$— and —C(=O)NH—(CH$_2$)$_n$—, wherein n is an integer from 1 to 20. In certain embodiments, $L_6$ is —C(=O)O—(CH$_2$)$_n$—, wherein n is 1-6.

In certain embodiments, $L_7$ is a C1-C20 alkylene chain. Representative $L_7$ groups include —(CH$_2$)$_n$—, where n is 1-20 (e.g., 1, 3, or 5)

In certain embodiments, $A_3$ is C, S, SO, P, or PO.

In certain embodiments, n is an integer from 5 to about 5,000.

In one embodiment, $R_7$, $R_8$, $R_9$, $R_{10}$, and $R_{11}$ are methyl, $L_6$ and $L_7$ are —C(=O)O—(CH$_2$)$_2$—, $A_1$ is C, and n is an integer from 10 to about 1,000.

In addition to the crosslinked copolymer (e.g., hydrogel) having repeating units having formula (VIII) above, the crosslinked polymer includes zwitterionic crosslinks having formula (III).

Representative crosslinked zwitterionic polymers of the invention have formula (IX):

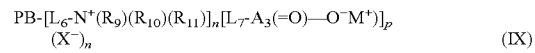
(IX)

wherein $L_6$, $N^+(R_9)(R_{10})(R_{11})$, $L_7$, $A_3(=O)OM$, $X^-$, n, and p are as described above, and PB is the polymer backbone that includes repeating units [formula (VIII)] and crosslinks [formula (III)].

The following is a description of the crosslinking agent, monomers, comonomers, polymers, copolymers, and crosslinks of formulas (I)-(IX) described above.

In the above formulas, PB is the polymer backbone. Representative polymer backbones include vinyl backbones (e.g., —C(R')(R")—C(R'")(R"")—, where R', R", R'", and R"" are independently selected from hydrogen, alkyl, and aryl) derived from vinyl monomers (e.g., acrylate, methacrylate, acrylamide, methacrylamide, styrene). Other suitable backbones include polymer backbones that provide for pendant groups. Other representative polymer backbones include peptide (polypeptide), urethane (polyurethane), and epoxy backbones.

Similarly, in the above formulas, CH$_2$=C(R)— is the polymerizable group. It will be appreciated that other polymerizable groups, including those noted above, can be used to provide the monomers and polymers of the invention.

In the above formulas, N$^+$ is the cationic center. In certain embodiments, the cationic center is a quaternary ammonium (e.g., N bonded to $L_4$, $R_5$, $R_6$, and $L_5$). In addition to ammonium, other useful cationic centers ($R_5$ and $R_6$ taken together with N) include imidazolium, triazaolium, pyridinium, morpholinium, oxazolidinium, pyrazinium, pyridazinium, pyrimidinium, piperazinium, and pyrrolidinium.

$R_4$, $R_5$, $R_6$, $R_9$, $R_{10}$, and $R_{11}$ are independently selected from hydrogen, alkyl, and aryl groups. Representative alkyl groups include C1-C10 straight chain and branched alkyl groups. In certain embodiments, the alkyl group is further substituted with one of more substituents including, for example, an aryl group (e.g., —$CH_2C_6H_5$, benzyl). Representative aryl groups include C6-C12 aryl groups including, for example, phenyl. For certain embodiments of the above formulas, $R_5$ and $R_6$, or $R_9$, $R_{10}$, and $R_{11}$ are taken together with $N^+$ form the cationic center.

$L_4$ (or $L_6$) is a linker that covalently couples the cationic center to the polymer backbone. In certain embodiments, $L_4$ includes a functional group (e.g., ester or amide) that couples the remainder of $L_4$ to the polymer backbone (or polymerizable moiety for the monomers). In addition to the functional group, $L_4$ can include an C1-C20 alkylene chain. Representative $L_4$ groups include —C(=O)O—$(CH_2)_n$— and —C(=O)NH—$(CH_2)_n$—, where n is 1-20 (e.g., 3).

$L_5$ is a linker that covalently couples the cationic center to the anionic group (i.e., (A=O)O$^-$). $L_5$ can be a C1-C20 alkylene chain. Representative $L_5$ groups include —$(CH_2)_n$—, where n is 1-20 (e.g., 1, 3, or 5).

$L_7$ is a linker that covalently couples the polymer backbone to the anionic group. $L_7$ can be a C1-C20 alkylene chain. Representative $L_7$ groups include —$(CH_2)_n$—, where n is 1-20 (e.g., 1, 3, or 5).

A(=O)—O$^-$ is the anionic center. The anionic center can be a carboxylic acid ester (A is C), a sulfinic acid (A is S), a sulfonic acid (A is SO), a phosphinic acid (A is P), or a phosphonic acid (A is PO).

In the above formulas, representative alkyl groups include C1-C30 straight chain and branched alkyl groups. In certain embodiments, the alkyl group is further substituted with one of more substituents including, for example, an aryl group (e.g., —$CH_2C_6H_5$, benzyl).

Representative aryl groups include C6-C12 aryl groups including, for example, phenyl including substituted phenyl groups (e.g., benzoic acid).

$X^-$ is the counter ion associated with the cationic center. The counter ion can be the counter ion that results from the synthesis of the cationic polymers or the monomers (e.g., Cl$^-$, Br$^-$, I$^-$). The counter ion that is initially produced from the synthesis of the cationic center can also be exchanged with other suitable counter ions to provide polymers having controllable hydrolysis properties and other biological properties. Representative hydrophobic counter ions include carboxylates, such as benzoic acid and fatty acid anions (e.g., $CH_3(CH_2)_nCO_2^-$ where n=1-19); alkyl sulfonates (e.g., $CH_3(CH_2)_nSO_3^-$ where n=1-19); salicylate; lactate; bis(trifluoromethylsulfonyl)amide anion ($N^-(SO_2CF_3)_2$); and derivatives thereof. Other counter ions also can be chosen from chloride, bromide, iodide, sulfate; nitrate; perchlorate ($ClO_4$); tetrafluoroborate ($BF_4$); hex afluorophosphate ($PF_6$); trifluoromethylsulfonate ($SO_3CF_3$); and derivatives thereof. Other suitable counter ions include hydrophobic counter ions and counter ions having therapeutic activity (e.g., an antimicrobial agent, such as salicylic acid (2-hydroxybenzoic acid), benzoate, lactate.

For the monomers, $R_1$ and $R_2$ [formula (I)] and $R_4$ [formula (IV)], is selected from hydrogen, fluoride, trifluoromethyl, and C1-C6 alkyl (e.g., methyl, ethyl, propyl, butyl). In one embodiment, $R_1$, $R_2$, and $R_4$ are hydrogen. In one embodiment, $R_1$, $R_2$, and $R_4$ are methyl.

Surfaces Treated with Crosslinked Zwitterionic Hydrogels

In another aspect, the invention provides surfaces that have been treated with crosslinked zwitterionic hydrogels. The crosslinked zwitterionic hydrogels of the invention, hydrolyzable to zwitterionic polymers, can be advantageously used as coatings for the surfaces of a variety of devices including, for example, medical devices.

The hydrogels of the invention are advantageously used to coat surfaces to provide biocompatible, antimicrobial, and nonfouling surfaces. Accordingly, in another aspect, the invention provides devices and materials having a surface (i.e., one or more surfaces) to which have been applied (e.g., coated, covalently coupled, ionically associated, hydrophobically associated) one or more crosslinked zwitterionic hydrogels of the invention. Representative devices and carriers that may be advantageously treated with a hydrogel of the invention, modified to include a hydrogel of the invention, or incorporates a hydrogel of the invention include:

particle (e.g., nanoparticle) having a surface treated with, modified to include, or incorporates a hydrogel of the invention;

drug carrier having a surface treated with, modified to include, or incorporates a material of the invention;

non-viral gene delivery system having a surface treated with, modified to include, or incorporates a hydrogel of the invention;

biosensor having a surface treated with, modified to include, or incorporates a hydrogel of the invention;

devices for bioprocesses or bioseparations, such as membranes for microbial suspension, hormone separation, protein fractionation, cell separation, waste water treatment, oligosaccharide bioreactors, protein ultrafiltration, and diary processing having a surface treated with, modified to include, or incorporates a hydrogel of the invention;

implantable sensor having a surface treated with, modified to include, or incorporates a hydrogel of the invention;

subcutaneous sensor having a surface treated with, modified to include, or incorporates by a hydrogel of the invention;

implant, such as a breast implant, cochlear implant, and dental implant having a surface treated with, modified to include, or incorporates a hydrogel of the invention;

contact lens having a surface treated with, modified to include, or incorporates a hydrogel of the invention;

tissue scaffold having a surface treated with, modified to include, or incorporates a hydrogel of the invention;

implantable medical devices, such as an artificial joint, artificial heart valve, artificial blood vessel, pacemaker, left ventricular assist device (LVAD), artery graft, and stent having a surface treated with, modified to include, or incorporates a hydrogel of the invention; and medical devices, such as an ear drainage tube, feeding tube, glaucoma drainage tube, hydrocephalous shunt, keratoprosthesis, nerve guidance tube, urinary catheter, tissue adhesive, and x-ray guide having a surface treated with, modified to include, or incorporates by a hydrogel of the invention.

Other representative substrates and surfaces that may be advantageously treated with a hydrogel of the invention, modified to include a hydrogel of the invention, or incorporates a hydrogel of the invention include fabrics and such as in clothing (e.g., coats, shirts, pants, undergarments, including such as worn by hospital and military personnel), bedding (e.g., blankets, sheets, pillow cases, mattresses, and pillows), toweling, and wipes.

Other representative substrates and surfaces that may be advantageously treated with a hydrogel of the invention, modified to include a hydrogel of the invention, or incorporates a hydrogel of the invention include working surfaces such as tabletops, desks, and countertops.

The following is a description of a representative zwitterionic crosslinked hydrogel of the invention (CBMA/CBMAX).

As noted above, the invention provides a zwitterionic crosslinker to improve the mechanical properties of nonfouling pCBMA hydrogels without the use of a fouling crosslinker. The structure of a representative zwitterionic crosslinker, a CBMA-based dimethacrylate crosslinker (CBMAX) is shown in FIG. 1, structure 3. The crosslinked has a chemical structure is identical to the CBMA monomer except that there is a one carbon spacer between the cationic quaternary amine and the anionic carboxyl group instead of two, and that one of the two methyl groups on the quaternary amine is replaced by a second methacrylate group. The crosslinker exhibits excellent solubility in 1M salt solutions, and its zwitterionic group ensures that, unlike MBAA, it will provide continuity of structured water across the crosslinks in a pCBMA hydrogel. The water structure of zwitterionic phosphorylcholine (PC)-based hydrogels made with a custom-made phosphorylcholine-based crosslinker was studied and a qualitative difference in the water in PC-crosslinked zwitterionic hydrogels compared to MBAA-crosslinked zwitterionic hydrogels was observed (Goda T, Watanabe J, Takai M, Ishihara K. Water structure and improved mechanical properties of phospholipid polymer hydrogel with phosphorylcholine centered intermolecular cross-linker. Polymer 2006; 47:1390-1396; and Goda T, Matsuno R, Konno T, Takai M, Ishihara K. Protein adsorption resistance and oxygen permeability of chemically crosslinked phospholipid polymer hydrogel for ophthalmologic biomaterials. J Biomed Mater Res B Appl Biomater 2009; 89:184-190). Hydrogels made from zwitterionic monomers and zwitterionic crosslinkers had more ice-like bound water than hydrogels made from zwitterionic monomers and MBAA, and the improved mechanical properties of the zwitterionically crosslinked zwitterionic hydrogels was attributed to the increased order of the water.

Figure 2:
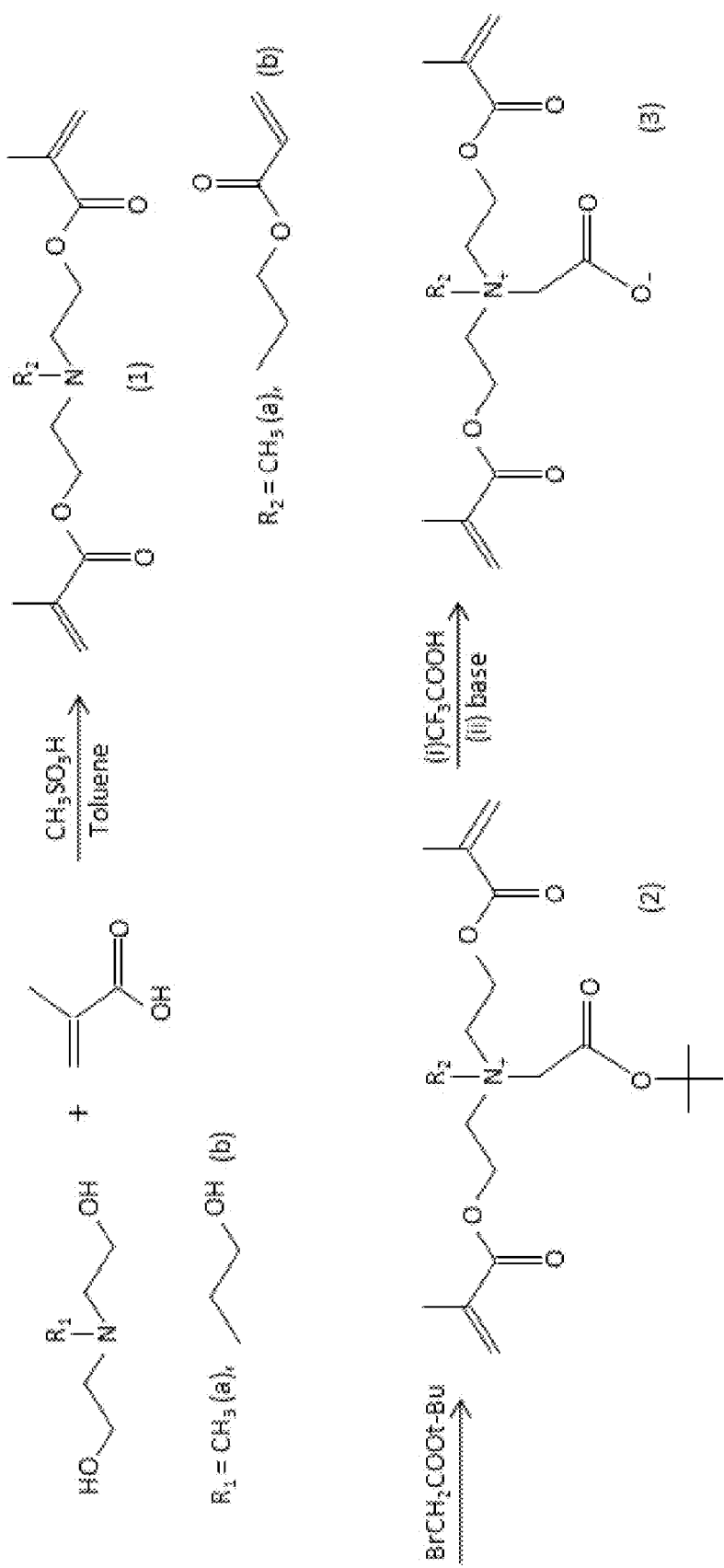
FIG. 2 is a schematic illustration of the synthesis of a representative zwitterionic crosslinker of the invention, carboxybetaine dimethacrylate (CBMAX) (3) and carboxybetaine dimethacrylate (CBMA3X) (4).

The preparation of a representative zwitterionic crosslinker of the invention, 1-carboxy-N-methyl-N-di(2-methacryloyloxy-ethyl)methanaminium inner salt (CBMX), is described in Example 1. The preparation is illustrated in FIG. 2

The preparation of a representative zwitterionic crosslinked hydrogel of the invention (CBMA/CBMAX) is described in Example 2.

The preparation and properties of representative zwitterionic crosslinked hydrogels of the invention, CBMA/CBMAX, prepared by photopolymerization are described in Example 3.

The preparation and properties of representative zwitterionic crosslinked hydrogels of the invention, CBMA/CBMAX, prepared by photopolymerization and having crosslinking gradients are described in Example 4.

The use of a representative zwitterionic crosslinked hydrogel of the invention, CBMA/CBMAX, in a glucose biosensor is described in Example 5.

Hydration Properties of CBMA Hydrogels with CBMAX

Figure 3A:
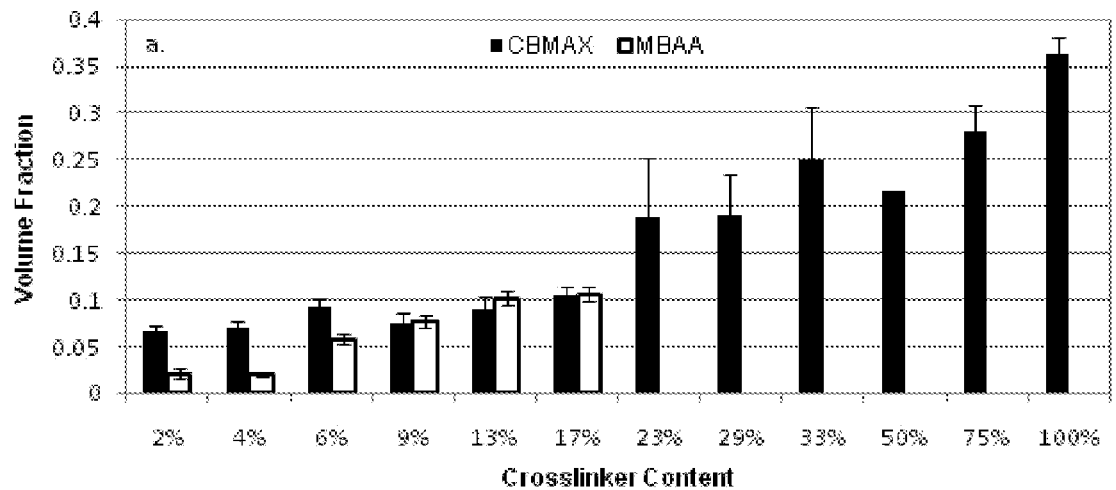
FIGS. 3A and 3B compare the hydration properties of representative zwitterionic crosslinked hydrogels of the invention, CBMAX-crosslinked CBMA hydrogels (CBMAX), to MBAA-crosslinked CBMA hydrogels (MBAA): volume fraction (FIG. 3A), the amount by volume of polymer in a swollen hydrogel; and equilibrium water content (EWC) (FIG. 3B), the amount by weight of water in the swollen hydrogel, as a function of crosslinker content (%). Closed bars represent CBMAX-crosslinked CBMA hydrogels, while open bars represent MBAA-crosslinked CBMA hydrogels.
Figure 3B:
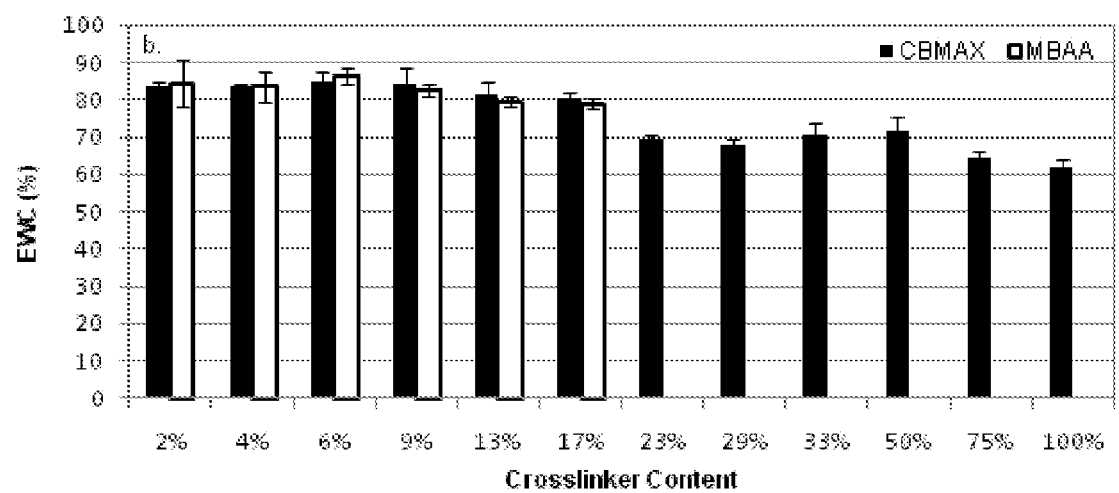

Because the high water content of hydrogels often mirrors the water content of biological tissues, hydrogels are attractive for biological applications, The swelling properties of CBMA hydrogels were calculated using equations (1) and (2): the mass and dimensions of hydrogel disks before and after dehydration were used to calculate the equilibrium water content and volume fraction of gels, respectively. FIGS. 3A and 3B show the equilibrium water content (FIG. 3A) and volume fraction (FIG. 3B) measured for MBAA-crosslinked hydrogels up to the solubility limit at 17% crosslinker and for CBMA-crosslinked hydrogels from 2% CBMAX to 100% CBMAX (open and closed bars, respectively). As expected, an increase in crosslinker content results in a decrease of hydration and swelling. At 100% CBMAX, hydration fell to about 60% equilibrium water content, a value that is remarkably high for such a large amount of crosslinking.

As these figures show, there appears to be no difference in water content when the CBMA is crosslinked with CBMAX or with MBAA.

Nonfouling Properties of CBMA Hydrogels with CBMAX

CBMA hydrogels made with 4% CBMAX, 4% MBAA, 17% CBMAX, and 17% MBAA, and CBMAX hydrogels, were tested for nonfouling. The low crosslinker content was chosen because it is the lowest that is practically handled, while the 17% crosslinker hydrogels were chosen because 17% is the upper limit of MBAA incorporation; this composition was expected to most clearly demonstrate any difference between the fouling properties of these two hydrogels. Fibroblast (COS-7) cells were seeded on antibiotic-sterilized hydrogels and allowed to grow for three days in supplemented growth medium. On the third day, cell adhesion was quantified visually: fifteen microscopy images of each hydrogel formulation were collected, and the absolute numbers of cells adhered to the gels were counted.

Figure 4:
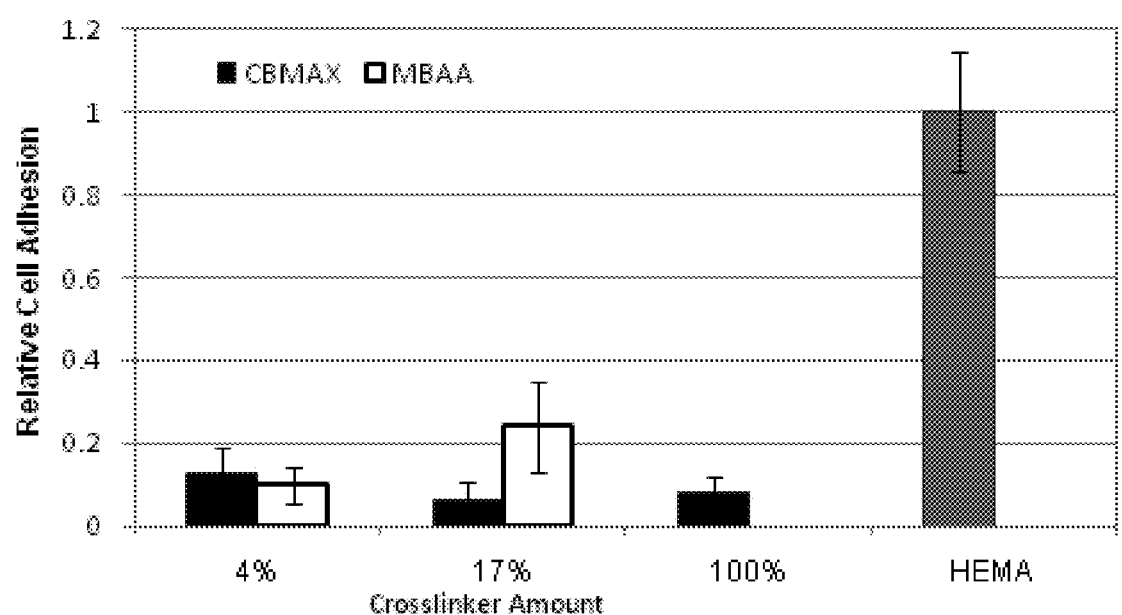
FIG. 4 compares relative cell adhesion as a function of crosslinker amount (%) for CBMAX- and MBAA-crosslinked CBMA hydrogels. Cell adhesion of CBMA hydrogels normalized to the cell adhesion of pHEMA hydrogels.

The number of cells adhered to hydrogels of each formulation are compared quantitatively in FIG. 4, as a function of crosslinker content, and normalized to the number of cells adhered to pHEMA hydrogels. Solid bars represent CBMAX-crosslinked hydrogels, while open bars represent MBAA-crosslinked hydrogels. The rightmost bar represents the control, pHEMA hydrogel. All CBMA hydrogels show a significant decrease (about 80-90%) in cell adhesion relative to low fouling pHEMA, especially in supplemented growth medium. pHEMA itself exhibits only a small percent of the cell adhesion on TCPS.

At low crosslinker content, both CBMAX- and MBAA-crosslinked hydrogels have very little fouling, about 10-15% that of pHEMA hydrogels (same within error). At higher crosslinker content there is a noticeable divergence: CBMAX-crosslinked hydrogels remain very nonfouling (about 10% that of pHEMA), while the fouling of MBAA-crosslinked hydrogels has worsened (to about 20% that of pHEMA). Furthermore, even 100% CBMAX hydrogels demonstrate the same low fouling levels of the lightly crosslinked CBMA hydrogels (about 10% that of pHEMA hydrogels). Thus, MBAA incorporation corrupts the nonfouling properties of CBMA hydrogels, possibly by disrupting the ordered water around the zwitterionic polymer chains, whereas the CBMA crosslinker provides continuity of chemistry and hydration of the molecular level, and thereby preserves the nonfouling properties within CBMA hydrogels. These results were supported by measuring the nonspecific protein adsorption via ELISA.

RGD-Functionalization of CBMA Hydrogels

Similar to the nonfouling study described above, CBMA hydrogels made using 17% CBMAX and 17% MBAA hydrogels demonstrate their ability for functionalization. The hydrogels were post-functionalized with cRGD, a cell-binding motif found on all integrins, using traditional EDC/sulfoNHS chemistry. Identical chemistry without EDC was performed on control hydrogels. COS-7 cells were then seeded on the EDC/sulfoNHS-cRGD-treated hydrogels, and on the sulfoNHS-cRGD-treated control hydrogels. The cell cultures were allowed to grow for 3 days, after which time cell proliferation was quantified with light microscopy.

Fifteen pictures were taken of each hydrogel formulation, and the absolute numbers of cells adhered to the gels were counted. The results are summarized in Table 1.

TABLE 1

Cell adhesion on 17% CBMAX- and MBAA-crosslinked hydrogels functionalized with cRGD. Nonspecific protein adsorption from ELISA reflects nonspecific cell adhesion on pre-functionalized hydrogels.

| Crosslinker (17%) | Protein Adsorption Nonspecific Protein Adsorption (ELISA, absorbance) | Cell Adhesion | |
|---|---|---|---|
| | | Cells Adhered Before Functionalization (abs. no./Frame) | Cells Adhered After Functionalization (abs. no./Frame) |
| CBMAX | 0.07 ± 0.03 | 2 ± 1 | 16 ± 3 |
| MBAA | 0.79 ± 0.02 | 10 ± 2 | 25 ± 3 |

As shown in Table 1, both functionalized CBMAX- and MBAA-crosslinked hydrogels exhibit an increase in cell adhesion. Nonspecifically adhered proteins from the supplemented medium will foul a surface and facilitate nonspecific cell adhesion. As shown by ELISA, CBMAX-crosslinked hydrogels resist nonspecific protein adsorption much more effectively than do MBAA-crosslinked hydrogels, and this is reflected in the lower overall number of cells adhered to the CBMAX-crosslinked hydrogels. The higher absolute numbers of adhered cells on 17% MBAA-crosslinked hydrogels, reflects the higher nonspecific cell adhesion, or fouling, that results from the presence of the MBAA. Both hydrogels are functionalized with cRGD to induce specific cell adhesion and demonstrate controlled biocompatibility. However, CBMAX-crosslinked hydrogels display lower levels of background nonspecific cell adhesion.

Mechanical Properties of CBMA Hydrogels

Mechanical properties are a major challenge for highly hydrated hydrogels. In general, the more water in the hydrogel, the weaker the structure. In order to function effectively as a mimic for biological tissue and to provide a conducive environment for cell growth, hydrogels should be "soft". Practically, however, mechanical strength is required for handling. Furthermore, substrate stiffness plays an important role in cell fate and stem cell differentiation.

Figure 5:
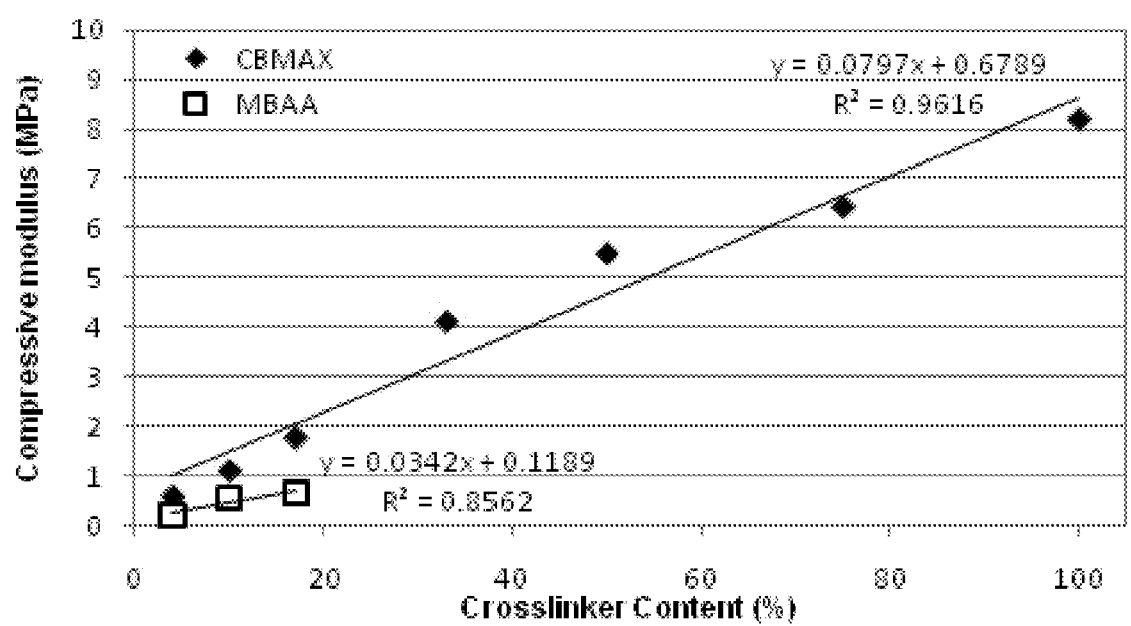
FIG. 5 compares compression modulus (MPa) of CBMAX- and MBAA-crosslinked CBMA hydrogels as a function of crosslinker content (%). Hydrogels were compressed to failure, and the modulus reported was taken from the first 10% strain. Closed diamonds represent CBMAX-crosslinked CBMA hydrogels, while open squares represent MBAA-crosslinked CBMA hydrogels.

Hydrogel disks were compressed to failure, and the extracted compressive Young's Moduli are shown in FIG. 5 as a function of crosslinker composition (CBMAX versus MBAA, represented by closed diamonds and open squares, respectively) and content (by % crosslinker). These values are also tabulated in Table 2.

At the crosslinker concentrations for which CBMAX- and MBAA-crosslinked hydrogels can be directly compared (4%, 9%, and 17%), the CBMAX-crosslinked hydrogels demonstrated improved mechanical properties. The compressive modulus of CBMAX-crosslinked hydrogels is greater than that of MBAA-crosslinked hydrogels at all concentrations accessible to both crosslinkers, and the break stress is greater at all concentrations as well. Higher crosslinker content is accessible with CBMAX. At 100% CBMAX, the compressive modulus reaches 8 MPa, an impressive value for a hydrogel with relatively high water content (60%), and one that places this material well within the range of articular cartilage. This also compares favorably to pHEMA hydrogels (compressive modulus of 0.6 MPa) and even to PEG hydrogels (compressive modulus up to about 3 MPa with 50% crosslinker water content).

Because no difference in the equilibrium water content of CBMA hydrogels with CBMAX versus CBMA hydrogels with MBAA crosslinker was found, these improved mechanical properties cannot be attributed to decreased hydration, but rather to a difference in the quality of the water structure.

The compression data demonstrates the linear nature of the relationship between the amount of crosslinker and the compressive modulus of the CBMA-CBMAX hydrogels. When compressive modulus is plotted as a function of crosslinker content from 4% crosslinker to 100% CBMAX (FIG. 5), the relationship is linear, and a regression of 0.9616. This underlines the compatibility of the gel system: the crosslinker is uniformly incorporated into the growing linear polymer chains at low crosslinker compositions, and, at the other end of the scale, the monomer is uniformly incorporated into the highly crosslinked network at high crosslink compositions. Thus, the hydrogel structure is more homogeneous. The MBAA crosslinker, on the other hand, showed poorer integration into the growing polymer chains, as evidenced by the less linear ($R^2$=0.8562) relationship between crosslinker composition and compressive modulus. Increasing the crosslinker content from 9% to 17% only marginally improved the mechanical properties of the gel, due to limited solubility even at this low concentration, and to poor incorporation of the dissolved crosslinker into the growing linear CBMA polymers. The microscopic structural defects that appear in inhomogeneous hydrogel networks compromise the mechanical integrity of the macroscopic hydrogel.

Physical Properties of CBMA Hydrogels

Using the hydration data and stress-stain curves collected above, equations 3 and 4 were used to calculate some physical properties of CBMA hydrogels when crosslinked

TABLE 2

Mechanical properties of CBMAX- and MBAA-crosslinked CBMA hydrogels. Modulus, break strain, and break stress, were extracted from stress-strain curves of CBMA hydrogels under compression.

Figure 6A:
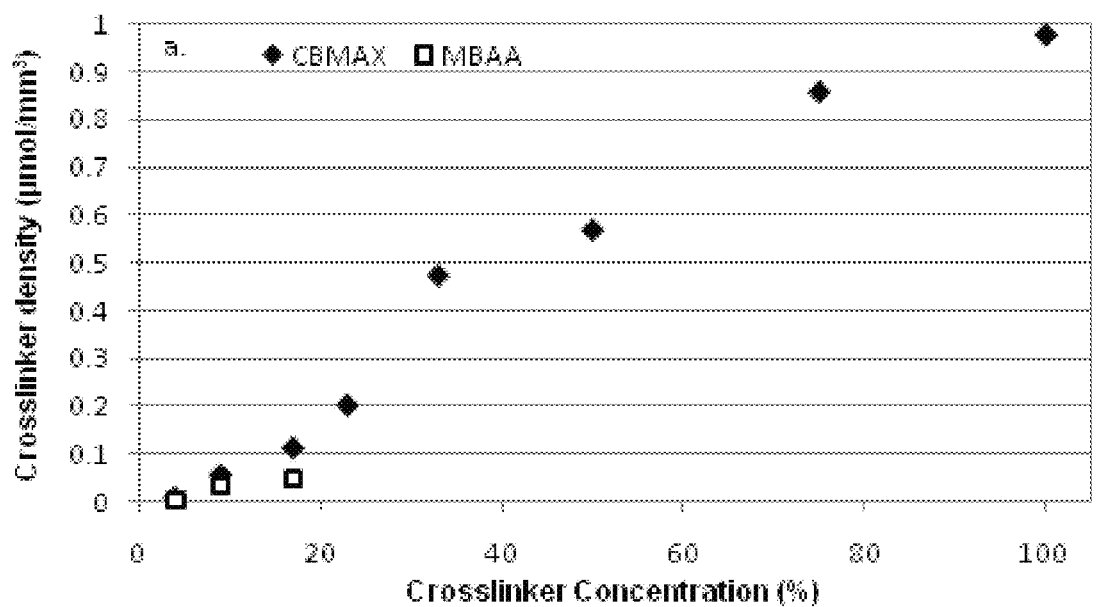
FIGS. 6A and 6B compare physical properties of CBMAX- and MBAA-crosslinked CBMA hydrogels: crosslinking density ($\mu mol/mm^3$) (FIG. 6A) and mesh size (nm) (FIG. 6B), each as a function of crosslinker concentration (%), calculated from mechanical and swelling properties. Closed diamonds represent CBMAX-crosslinked CBMA hydrogels, while open squares represent MBAA-crosslinked CBMA hydrogels.
Figure 6B:
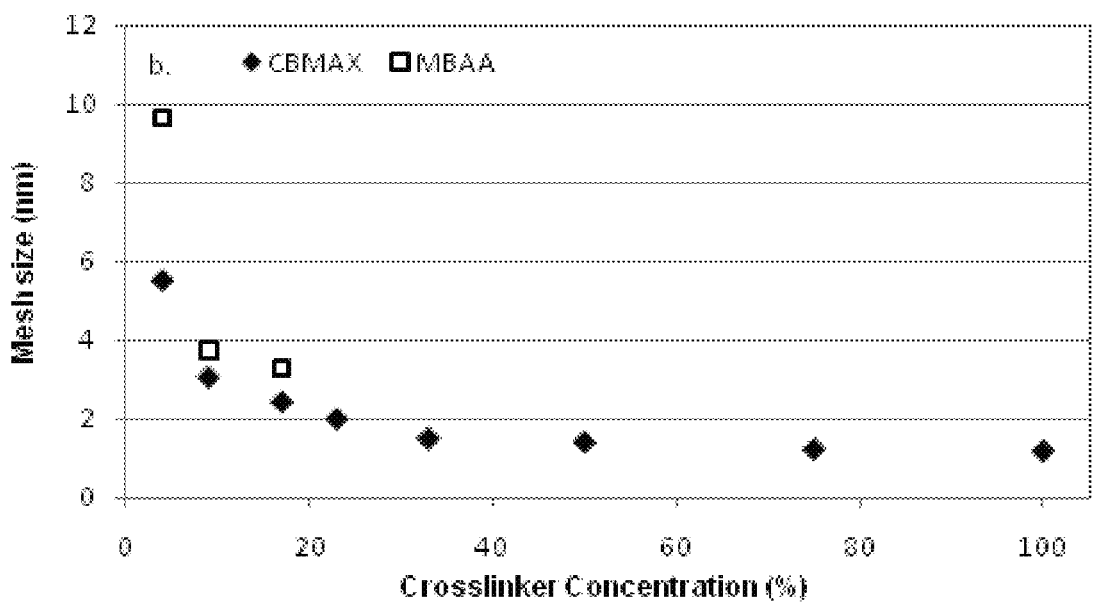

| Crosslinker content (%) | Modulus (MPa) | | Break strain (%) | | Break stress (MPa) | |
|---|---|---|---|---|---|---|
| | MBAA | CBMAX | MBAA | CBMAX | MBAA | CBMAX |
| 4 | 0.20 ± 0.03 | 0.6 ± 0.1 | 40 | 30 | 0.06 | 0.1 |
| 9 | 0.57 ± 0.03 | 1.11 ± 0.06 | 45 | 25 | 0.3 | 0.4 |
| 17 | 0.65 ± 0.06 | 1.79 ± 0.09 | 30 | 30 | 0.3 | 0.6 |
| 33 | — | 4.1 ± 0.6 | — | 25 | — | 0.6 |
| 50 | — | 5.5 ± 0.3 | — | 20 | — | 1 |
| 75 | — | 6.44 ± 0.02 | — | 15 | — | 1 |
| 100 | — | 8.2 ± 0.5 | — | 45 | — | 2.5 | with MBAA or CBMAX. Specifically, the stress-strain curves are manipulated to stress vs. ($\alpha$-$\alpha^{-2}$) curves, where a is the ratio of the deformed length to the original length. At low strains, this relationship is linear, and the crosslinking density can be extracted from the slope of this line (see equation 3). Then, converting the number of crosslinks per volume to the volume per single crosslinker yields the distance between two crosslinks. These calculated values of crosslinker density and mesh size, as a function of crosslinking composition and content, are shown in FIGS. 6A and 6B, respectively. It can be seen that at the same nominal crosslinker content, the crosslinking densities of MBAA-crosslinked hydrogels is lower than that of CBMAX-crosslinked hydrogels, reinforcing the hypothesis that MBAA is less compatible with the CBMA monomer and thus the acrylamides of the MBAA incorporate poorly into the growing methacrylate polymer chains. On the other hand, the higher crosslinker density of the CBMAX-crosslinked hydrogels suggests better compatibility and more uniform incorporation of the CBMAX methacrylates into the growing methacrylate polymer. The mesh sizes calculated from the crosslinker density values tell a similar story, and further support the idea that the difference in the monomer-crosslinker compatibility plays a major role in the difference in the mechanical properties of the CBMA-CBMAX and CBMA-MBAA systems.

Additionally, due to its excellent solubility and copolymerization with the CBMA monomer, the CBMAX-crosslinked hydrogels have access to a wider range of formulations, which provides greater diversity of physical properties. The different crosslinking densities, and thus different pore sizes, that arise in a controlled manner with CBMAX-crosslinked hydrogels afford yet another means of biological manipulation. Hydrogels are prized for their biomimetic structure: high water content and pores that allow passage of biomolecules. Pores ranging in size from <2 nm for small molecules such as sugars and growth factors, to pores >10 nm for biomacromolecules such as large proteins and antibodies render all accessible to incorporation into hydrogels. By controlling the crosslinker content, the pore size of the hydrogels can be controlled without compromising nonfouling properties.

The zwitterionic crosslinker of the invention has excellent compatibility with zwitterionic hydrogel systems. A representative crosslinker, CBMAX, has a structure that corresponds to a useful zwitterionic monomer, CBMA, which provides two advantageous effects. First, the zwitterionic nature of the crosslinker means that, in addition to the improved solubility, the crosslinker does not interrupt the restructuring of water that occurs around the zwitterionic monomer sidechains. Compared to hydrogels crosslinked with MBAA, CBMAX-crosslinked hydrogels exhibited improved nonfouling at all compositions accessible to MBAA-crosslinked hydrogels, and ultimately demonstrated only about 10% of the nonspecific protein adsorption of pHEMA hydrogels. Second, the chemical similarity between the CBMA monomer and CBMAX crosslinker provides great polymerization compatibility. CBMAX-crosslinked hydrogels showed apparent stoichiometric incorporation of monomers and crosslinker. On the other hand, as MBAA-crosslinked hydrogels reached the solubility limit of MBAA, the relationship between crosslinker content and compressive modulus began to fail. Thus, CBMAX-crosslinked hydrogels exhibited greatly improved mechanical properties relative to MBAA-crosslinked hydrogels at the same nominal crosslinker content. The water solubility of the CBMAX crosslinker, additionally, allows access to a much wider range of formulations than were previously possible. Hydrogels made by polymerizing only the crosslinker (in the absence of monomer) were found to have high water content (60%), excellent nonfouling properties (about 90% lower nonspecific cell adhesion than the nonfouling pHEMA control hydrogel), and high mechanical strength (compressive modulus of about 8 MPa). Furthermore, these hydrogels composed of the CBMAX crosslinker, like those made with the CBMA monomer, are functionalizable by means of simple EDC/sulfoNHS chemistry.

The follow examples are provided for the purpose of illustrating, not limiting, the invention.

EXAMPLES

Materials.

N,N'-Methylenebis(acrylamide), ammonium persulfate, sodium metabisulfite, 2-(N-morpholino)ethanesulfonic acid (MES), methacrylic acid, ion exchange resin (IRA 400 OH form), and phosphate-buffered saline were purchased from Sigma Aldrich (St. Louis, Mo.). Ethanol was purchased from Decon Labs (King of Prussia, Pa.), acetonitrile and diethyl ether from EMD Biosciences (Gibbstown, N.J.), ethylene glycol from VWR (West Chester, Pa.), tetraethylene glycol dimethacrylate from Polysciences (Warrington, Pa.), 2-hydrolxyethyl methacrylate, t-butyl bromoacetate, and N-cyclohexyl-2-aminoethanesulfonic acid (CHES) from TCI America (Portland, Oreg.), and N,N,N',N'-tetramethylethylenediamine (TEMED) from Bio-Rad Laboratories (Hercules, Calif.). N-Methyldiethanolamine, triethanolamine, methanesulfonic acid, and trifluoroacetic acid were purchased from Acros Organics (Morris Plains, N.J.). Dulbecco's Modified Eagle Medium, fetal bovine serum, nonessential amino acids, and penicillin-streptomycin were purchased from Invitrogen Corp (Carlsbad, Calif.). Cyclo (arginine-glycine-asparginine-D-tyrosine-lysine) peptide (cRGD) was purchased from Peptides International (Louisville, Ky.). Hydrogen peroxide and sodium chloride salt were purchased from J.T. Baker (Phillipsburg, N.J.), and ImmunoPure® o-Phenylenediamine dihydrochloride was purchased from Pierce (Rockford, Ill.). Horseradish peroxidase (HRP)-conjugated anti-fibrinogen was purchased from US Biological (Swampscott, Mass.). COS-7 cells (African Green Monkey fibroblast cells) were purchased from the American Tissue Culture Collection (Manassas, Va.). All water used had been purified to 18.2 mΩ on a Millipore Simplicity water purification system.

Example 1

The Preparation of Representative Zwitterionic Crosslinkers: 1-Carboxy-N-methyl-N-di(2-methacryloyloxy-ethyl)methanaminium inner salt (CBMX) and 1-Carboxy-N-tri(2-methacryloyloxy-ethyl)methanaminium inner salt (CBMA3X)

In this example, the preparation of representative zwitterionic crosslinkers of the invention, 1-carboxy-N-methyl-N-di(2-methacryloyloxy-ethyl)methanaminium inner salt (CBMX) and 1-carboxy-N-tri(2-methacryloyloxy-ethyl) methanaminium inner salt (CBMA3X), are described. The preparations are illustrated in FIG. 2.

N-Methyl-N-di(ethanolamine methacrylate) (1)

N-Methyldiethanolamine (11.9 g, 0.1 mol), toluene (100 ml), hydroquinone (2.0 g), and methacrylic acid (21.5 g, 0.25 mol) were added to a 500 ml reaction flask fitted with a stirrer, condenser, and Dean-Star trap. Methanesulfonic acid (14.4 g, 0.15 mol) was added slowly and the mixture was heated to reflux. After the theoretical water of reaction was collected azeotropically, the solution was cooled to room temperature. The mixture was then neutralized with 25 wt % aqueous sodium hydroxide and the organic phase was washed with 10% brine solution and dried over anhydrous magnesium sulfate. The solution was filtered, and the filtrate was further treated with activated carbon and basic alumina. The resulting solution was removed under vacuum to give a colorless oil with 73% yield. $^1$H-NMR (DCDl$_3$) δ: 6.10 (s, 2H), 5.56 (s, 2H), 4.25 (t, J=6.0 Hz, 4H), 2.78 (t, J=6.0 Hz, 4H), 2.39 (s, 3H), 1.94 (s, 6H).

N-Methyl-N-di(2-methacryloyloxy-ethyl)-N-1-(t-butyloxycarbonylmethyl) ammonium bromide (2)

Compound (1) (12.75 g, 50 mmol), t-butyl bromoacetate (11.70 g, 60 mmol), acetonitrile (100 ml) were mixed in a nitrogen-filled flask. The mixture was stirred at 60° C. for 2 days. The solvent was evaporated under vacuum and the residue was washed with ether and dried to obtain a white solid with 90% yield. $^1$H-NMR (DCDl$_3$) δ: 6.15 (s, 2H), 5.67 (s, 2H), 4.80 (s, 2H), 4.73 (t, J=6.0 Hz, 4H), 4.47 (m, 4H), 3.75 (s, 3H), 1.95 (s, 6H), 1.48 (s, 9H).

1-Carboxy-N-methyl-N-di(2-methacryloyloxy-ethyl) methanaminium inner salt (3) (CBMAX)

The t-butyl ester moiety of compound (2) (13.5 g, 30 mmol) was removed by treatment with trifluoroacetic acid (TFA, 30 ml) in dichloromethane (120 ml) for 2 days at room temperature. The solvent was removed under vacuum and replaced with acetonitrile (120 ml). The solution was neutralized over an ion exchange resin (IRA 400 OH form), subsequently concentrated and precipitated into ether, and finally vacuum dried to obtain a white solid with quantitative yield. $^1$H-NMR (D$_2$O) δ: 6.05 (s, 2H), 5.66 (s, 2H), 4.56 (t, 4H), 4.20 (m, 2H), 3.95 (m, 4H), 3.24 (s, 3H), 1.83 (s, 6H).

1-Carboxy-N-tri(2-methacryloyloxy-ethyl)methanaminium inner salt (4) (CBMA3X)

Compound (4) was prepared using a similar method as CBMAX, from triethanolamine and methacrylic acid to give to N-tri(ethanolamine methacrylate), then react with t-butyl bromoacetate to give N-tri(2-methacryloyloxy-ethyl)-N-1-(t-butyloxycarbonylmethyl) ammonium bromide. After removal of the t-butyl ester moiety to obtain compound 4 as a white solid. $^1$H-NMR (D$_2$O) δ: 6.07 (s, 3H), 5.70 (s, 3H), 4.60 (t, 6H), 4.20 (t, 6H), 4.04 (s, 2H), 1.85 (s, 9H).

Example 2

The Preparation and Properties of Representative Zwitterionic Crosslinked Hydrogels: CBMA/CBMAX In this example, the preparation of representative zwitterionic crosslinked hydrogels of the invention, CBMA/CBMAX, is described. The properties of a zwitterionic CBMAX-crosslinked hydrogel (CBMA/CBMAX) were compared to a zwitterionic MBAA-crosslinked hydrogel (CBMA/MBAA).

2-Carboxy-N,N-dimethyl-N-(2'-(methacryloyloxy)ethyl) ethanaminium inner salt (carboxybetaine methacrylate, CBMA) was synthesized as described in Zhang Z, Chao T, Chen S, Jiang S. Superlow fouling sulfobetaine and carboxybetaine polymers on glass slides. Langmuir 2006; 22(24):10072-10077.

Hydrogel Preparation

Monomer solutions were prepared in 1M NaCl, at a monomer concentration of 65% by weight. To these solutions, the crosslinkers (N',N'-methylenebis(acrylamide) (MBAA) or CBMAX (prepared as described in Example 1) was added at amounts ranging from 2-23% (molar percent of monomer). CBMAX formulations above this were prepared up to 75% by maintaining a constant total molar amount of monomer and crosslinker, and adjusting their relative molar amounts. 100% CBMAX was simply prepared by dissolving the desired amount of CBMAX in 1M NaCl. The solutions were mixed by sonication. In some cases (above about 10% MBAA), the crosslinker did not dissolve completely. A 40% solution of ammonium persulfate and 15% sodium metabisulfite were added to the solution to initiate polymerization. The solutions were polymerized between glass microscope slides separated by 0.5 or 2 mm-thick polytetrafluoroethylene (PTFE) spacers at 60° C. The gels were then removed from the slides and immersed in phosphate-buffered saline (PBS) to hydrate. This hydration water was changed daily for 5 days to remove unreacted chemicals and excess salt. Biopsy punches were used to punch hydrated hydrogels into 5 mm-diameter disks. HEMA hydrogels were prepared by mixing 0.78 ml HEMA monomer in 1.5 ml of a mixed solvent comprised of 1 part ethanol, 1.5 parts ethylene glycol, and 1.5 parts water. The crosslinker, tetraethylene glycol dimethacrylate (TEGDMA), was then added (60 μl), and the resulting solution was sonicated to mix well. Finally, 24 μl 40% ammonium persulfate and 7.5 μl TEMED were added. This hydrogel was formed as described above.

Swelling Properties of Hydrogels

Hydrogels were allowed to swell to equilibrium in PBS for five days. Disks with 0.5-cm diameter were cut from the swollen gel cast at 0.5 mm thickness. The disks were weighed and then dehydrated under vacuum at 50° C. and 30 in. Hg vacuum for 3 days. Dried hydrogel disks were measured with a caliper and weighed. The volume fraction (Φ) of polymer within a swollen hydrogel is given by:

$$\varphi_2 = \left(\frac{D_o}{D}\right)^3 \quad (1)$$

where $D_o$ and D are the diameters of dried and swollen disks, respectively. The volume fraction of polymer in the relaxed (unswollen) hydrogel, $\phi_o$, was determined from the monomer/crosslinker solutions. The volume of the solution was compared to the volume of water added. The difference in volume was taken as the volume of monomer, which corresponds to the volume of polymer after polymerization.

The equilibrium water content values were determined as:

$$EWC = 100(\%) * \frac{m_w - m_d}{m_w} \quad (2)$$

where $m_w$ is the mass of the wet hydrogel and $m_d$ is the mass of the dry hydrogel.

All samples were measured in triplicate.

Protein Adsorption Evaluated by Enzyme-Linked Immunosorbent Assay (ELISA)

To measure fibrinogen adsorption, hydrogel disks of 0.5 cm diameter (0.5 mm thickness when cast) were incubated with 1 mg/ml fibrinogen in a well plate for 15 minutes at room temperature followed by washes with PBS buffer over 4 hours. The hydrogels were then removed from the last PBS wash and transferred to new wells. They were next incubated with a 1:500-dilution of horseradish peroxidase (HRP)-conjugated anti-fibrinogen in PBS for 10 minutes followed by another 5 washes with the same buffer. The hydrogels were then washed repeatedly with PBS buffer for 4 hours, removed from the last wash, and transferred to new wells. Finally, 500 µl 1 mg/ml o-phenylenediamine hydrochloride (OPD) in 0.1 M citrate-phosphate buffer, pH 5.0, containing 0.03% hydrogen peroxide, was added to each hydrogel at 30-second intervals. The samples incubated in the OPD solution for 30 minutes away from light. The supernatant was removed from each hydrogel disk, transferred to a cuvette, and its absorbance at 492 nm was measured. All samples were measured in triplicate.

Cell Adhesion to Hydrogels

Three hydrogel disks of 0.5 cm diameter (0.5 mm thickness when cast) were placed individually in the wells of a 48-well plate with 500 ul PBS solution. To sterilize the hydrogels, they were irradiated with UV light for 30 minutes and refrigerated overnight in 1× penicillin-streptomycin in PBS. COS-7 cells (p=7) were seeded onto the hydrogels at a concentration of $10^4$ cells/ml in supplemented Dulbecco's Modified Eagle Medium. Cells were allowed to grow for 72 hours at 37° C., 5% $CO_2$, and 100% humidity, after which time the hydrogels were photographed at 10× magnification on a Nikon Eclipse TE2000-U microscope. Photographs were taken at five predetermined areas on the surface of the hydrogel, for a total of fifteen images per hydrogel formulation, and the number of adherent cells from each image was totaled and normalized to the number of cells adhered to pHEMA hydrogels.

RGD Functionalization Via EDC/sulfoNHS Chemistry

CBMA/MBAA and CBMA/CBMAX gels were functionalized with cRGD. Three hydrogel disks of 0.5 cm diameter (0.5 mm thickness when cast) were placed in the wells of a 24-well plate. All gels of each formulation were split into two groups. The gels of each group were placed in the same well, with care taken to ensure that the surface of each hydrogel was uncovered. The hydrogels were incubated in 500 µl MES buffer solution (pH=5.5, 10 mM MES, 100 mM NaCl) overnight. The MES was then removed from one group of each formulation and replaced with 500 µl of an MES-based buffer solution containing 5 mM sulfoNHS and 100 mM EDC, to activate the surface, for 2 hours at room temperature. As a control, the second group of each formulation was incubated with an MES-based buffer solution of 5 mM sulfoNHS, for the same amount of time. The EDC/sulfoNHS and sulfoNHS solutions were then removed from the wells, and the hydrogel disks were washed three times with MES buffer. To all wells was next added 500 µl 1.4 mM cRGD in CHES buffer (pH=9, 50 mM CHES, 100 mM NaCl), and the reaction was allowed to proceed at room temperature. After 3 hours, the hydrogels were washed three times with PBS, allowing 10 minutes per wash. Finally, hydrogels were transferred to individual wells of a 48-well polystyrene tissue culture plate, with care taken that the functionalized surface remained facing upwards. The hydrogels were sterilized with penicillin-streptomycin overnight as described above, and cell adhesion was performed the next day, also as described above.

Mechanical Strength of Hydrogels

At least five 0.5 cm diameter disks of each formulation (2 mm thickness when cast) were compressed to failure at a rate of 1 mm/min using an Instron 5543A mechanical tester (Instron Corp., Norwood, Mass.) with a 10N load cell. The Young's modulus was calculated from the initial 10% strain.

Calculation of Physical Properties of CBMA hydrogels

Hydrogel hydration properties (swollen and relaxed volume fractions) and stress-strain curves can be used to calculate the crosslinker density and mesh size of the different 2-arm CBMAX- and MBAA-crosslinked hydrogel formulations. To calculate the crosslinker density (va/V) of hydrogels, the following equation was used:

$$\tau_S = \left(\frac{v_e}{V}\right)\frac{RT(\alpha - \alpha)^{-2}}{(\varphi_2/\varphi_0)^{2/3}} \quad (3)$$

where $\tau_s$ is the stress at a particular strain, in units of Pa, $\alpha$ is the deformation ratio, or the ratio of the deformed length to the original length of a crosslinked hydrogel under compression. R is the universal gas constant, T is absolute temperature, $\phi_2$ is the volume fraction of polymer at equilibrium (in the fully swollen hydrogel), and $\phi_o$ is the volume fraction of polymer in the relaxed state (unswollen, but not dehydrated, hydrogel). A plot of $\tau_s$ vs $(\alpha-\alpha^{-2})$ is linear at low strain, and the crosslink density $(v_e/V)$ can be extracted from the slope $(v_e/V)(RT)(\phi_2/\phi_o)^{-2}$.

The crosslink density in moles/unit volume can be converted to distance between crosslinks, or mesh size, using equation (4):

$$\xi = \left(\frac{N_A v_e}{V}\right)^{1/3} \quad (4)$$

where $N_A$ is Avogadro's number. Equation (4) inverts moles/volume to volume per mole, converts moles to number of crosslinks, and takes a cube root to obtain distance per crosslink. This value is effectively pore size of the hydrogel.

Example 3

The Preparation and Properties of a Representative Zwitterionic Crosslinked Hydrogels Prepared by Photopolymerization: CBMA/CBMAX In this example, the preparation and properties of representative zwitterionic crosslinked hydrogels of the invention, CBMA/CBMAX, prepared by photopolymerization are described.

Preparation of CB-Based Hydrogels

Solutions of monomer and crosslinker were prepared in 1M NaCl, with 47% polymerizable material by weight. The crosslinker (CBMAX) was included at amounts ranging from 2-80 mole % of monomer (CBMA). A solution for 100% CBMAX was prepared by dissolving the desired amount of CBMAX in 1M NaCl, with 47 wt % CBMAX. All solutions were mixed by sonication in ice water. 1% (wt/wt) of photoinitiator, 2-hydroxy-2-methyl-1-phenyl-1-propanone, was added to each solution and sonication in ice water was used to mix the solution thoroughly. The solutions were polymerized between glass microscope slides separated by 1 mm-thick polytetrafluoroethylene (PTFE) spacers with UV irradiation, 365 nm, for 30 minutes on each side. The gels were then removed from the slides and immersed in PBS to hydrate. This hydration water was changed daily for 5 days to remove unreacted chemicals and excess salt. Biopsy punches were used to punch hydrated hydrogels into 5 mm-diameter disks.

Hydration Properties of Hydrogels

Figure 7:
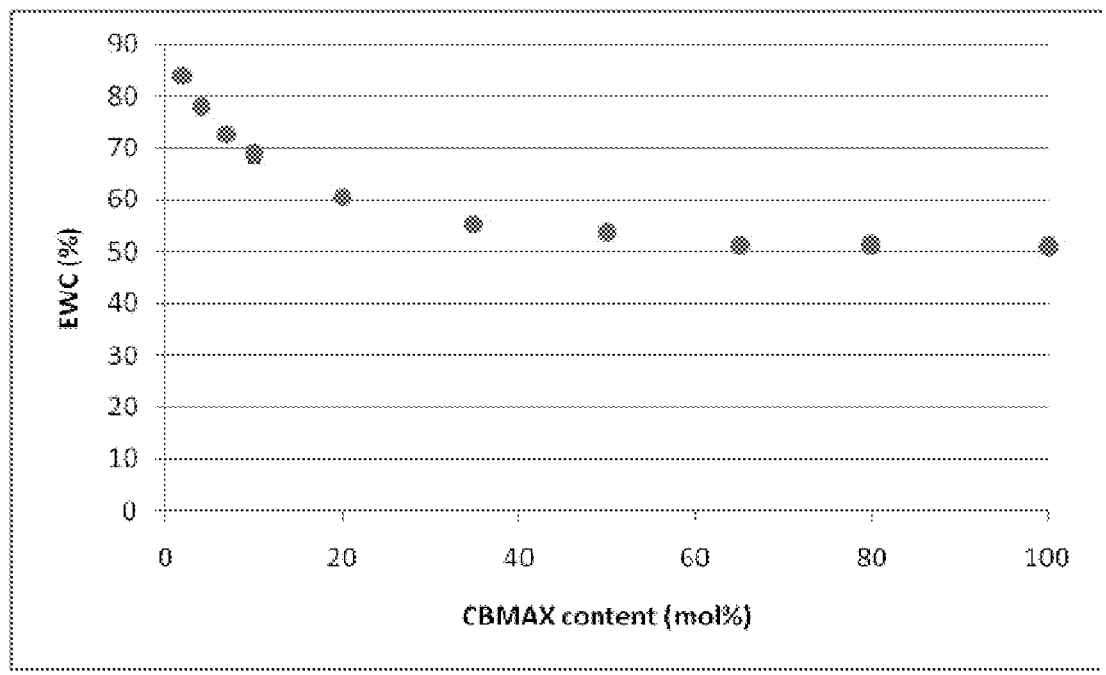
FIG. 7 compares the hydration properties (EWC) as a function of crosslinker content (mol %) of representative zwitterionic crosslinked polymers of the invention, CBMA/CBMAX, prepared by photopolymerization.

Swollen hydrogel disks were equilibrated in PBS for five days. 0.5 cm disks were cut from the fully hydrated hydrogel slabs and weighed. The disks were then dehydrated in a vacuum oven at 45° C. and 30 in. Hg vacuum for 3 days. The swelling ratios were determined by the ratio of the swollen hydrogel weight to the dry hydrogel weight and the equilibrium water content (EWC) of each disk was determined as EWC=100(%)*$(m_w-m_d)/m_w$, where $m_w$ is the mass of the wet hydrogel and $m_d$ is the mass of the dry hydrogel. All samples were measured in triplicate. EWC values for CBMA-CBMAX hydrogels with varying CBMAX content are shown in FIG. 7. As the gels become more crosslinked, the EWC decreases until reaching a steady value of approximately 51% for gels containing more than 50 mol % CBMAX.

Compressive Properties of Hydrogels

Figure 8:
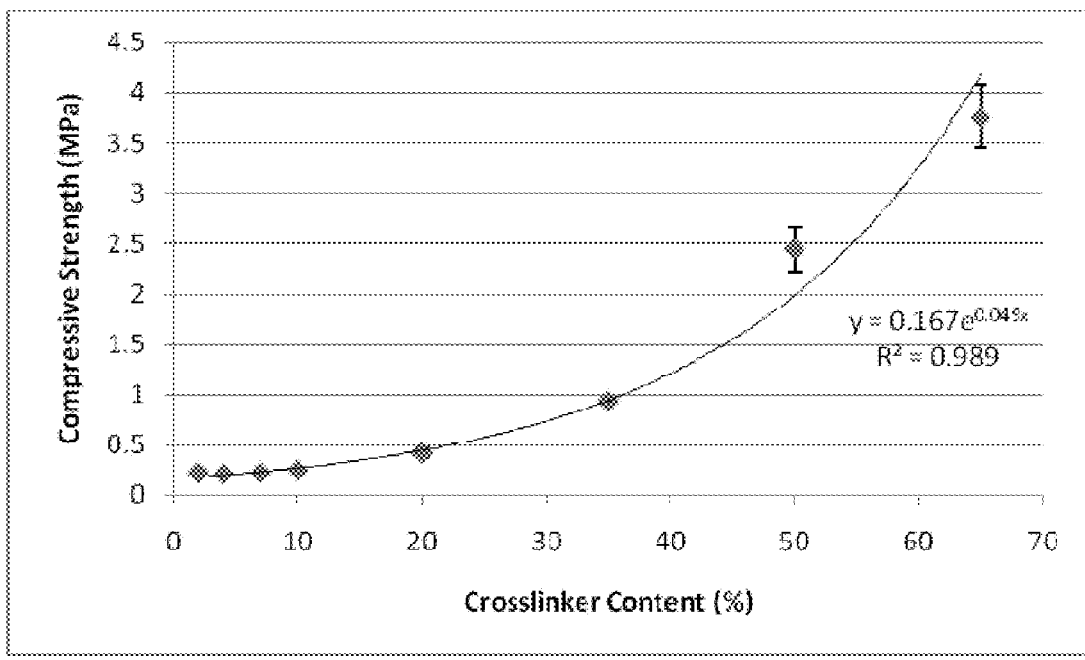
FIG. 8 compares the compressive strength (MPa) as a function of crosslinker content (%) of representative zwitterionic crosslinked polymers of the invention, CBMA/CBMAX, prepared by photopolymerization.
Figure 9:
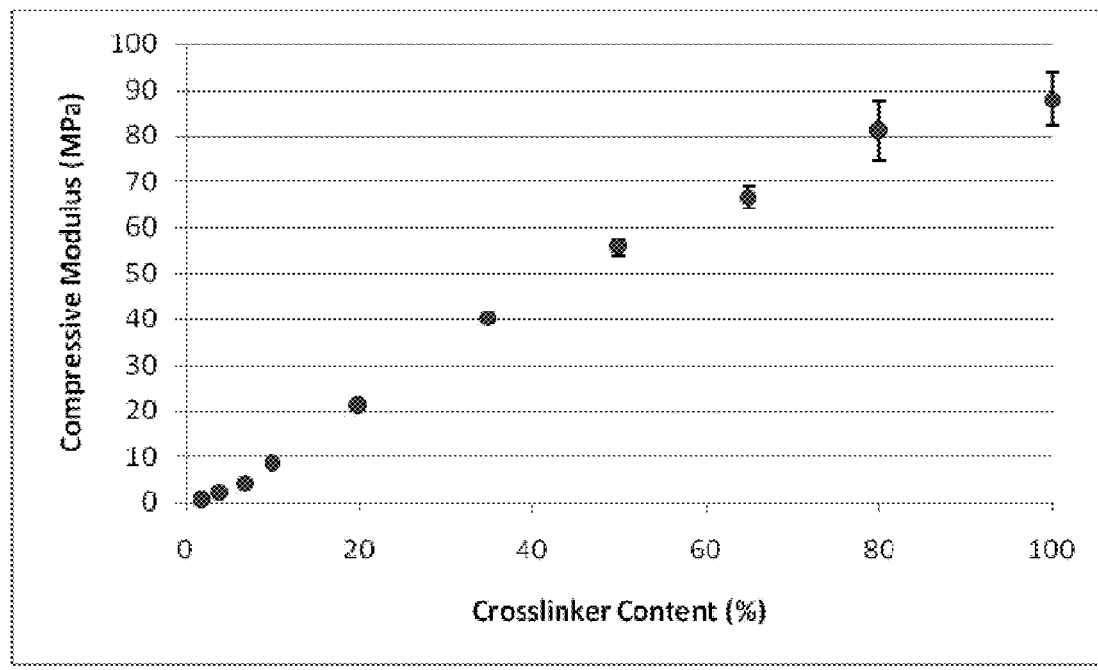
FIG. 9 compares the compressive modulus (MPa) as a function of crosslinker content (%) of representative zwitterionic crosslinked polymers of the invention, CBMA/CBMAX, prepared by photopolymerization.

At least three disks of 0.5 cm diameter (1 mm thickness when cast) were compressed to failure at a rate of 1 mm/min using an Instron 5543A mechanical tester (Instron Corp., Norwood, Mass.) with a 10N load cell. The Young's modulus was calculated from the initial 10% strain. FIGS. 8 and 9 show the compressive strength and modulus, respectively, of CBMA-CBMAX hydrogels with varying CBMAX incorporation. The compressive strength and modulus of the gels increase as crosslinker content increases. The trend in modulus is identical to hydrogels that are synthesized via thermal initiation, however there is a 10-fold increase in value. The decreased modulus values for thermally polymerized hydrogels could be due to inhomogeneities across the gel as a result of heat transfer limitations during initiation. Pockets of inhomogeneity will adversely affect mechanical properties. An alternate explanation for the increase in modulus for photopolymerized gels could stem from the solubility of the photoinitiator. The photoinitiator is less water soluble than the thermal initiator, so fewer polymer chains will be initiated. This translates into longer polymer chains, which is the same as having more cros slinks in hydrogels.

Cytotoxicity and Endotoxicity Testing of Hydrogels

The photopolymerized CBMAX-crosslinked CBMA hydrogels were tested to ensure that they contain neither cytotoxic chemical features or endotoxin contamination. Materials prepared for in vivo implantation must be free of endotoxins, which are bacterial residues from the cell wall of Gram-negative bacteria. In vitro bacterial residues are inconsequential, but in vivo they can trigger an immune response that will enhance the foreign-body response against the material and confound the results of in vivo testing.

To test for cytotoxicity, fully-hydrated hydrogel disks were soaked in supplemented growth medium (89% Dulbecco's Modified Eagle Medium, 10% fetal bovine serum, 1% penicillin-streptomycin, and 1× non-essential amino acids) for 24 hours, whereupon the medium was removed from the hydrogels and used to culture COS-7 cells that had been plated and grown in fresh supplemented medium 24 hours prior. The cells were then incubated with the hydrogel-infused supplemented medium for a further 48 hours, and their morphology was analyzed as an indicator of cell proliferation and health. It was found that all of the cell populations displayed the same degree of proliferation and health whether they were incubated with hydrogel-infused medium or with a fresh medium control.

To test for endotoxin contamination, a Limulus Amebocyte Lysate (LAL) endotoxin test was performed, following a standard procedure. Samples were extracted with LAL-free water for several days and the water was then tested for the presence of endotoxins using an enzymatic assay with sensitivity to detect endotoxins above 0.06 EU/ml (Lonza). In the presence of endotoxins at concentrations this detection limit, the enzyme assay solution will crosslink itself to form a gel, but gelation will not occur at endotoxin levels below this concentration. Standards were tested alongside the samples to validate the results. The gelation assay revealed that all of the hydrogels tested were free of endotoxins.

Example 4

The Preparation and Properties of a Representative Zwitterionic Crosslinked Hydrogels Prepared by Photopolymerization Having Crosslinking Gradients: CBMA/CBMAX In this example, the preparation and properties of representative zwitterionic crosslinked hydrogels of the invention, CBMA/CBMAX, prepared by photopolymerization and having crosslinking gradients are described.

Hydrogel Preparation

Figure 10:
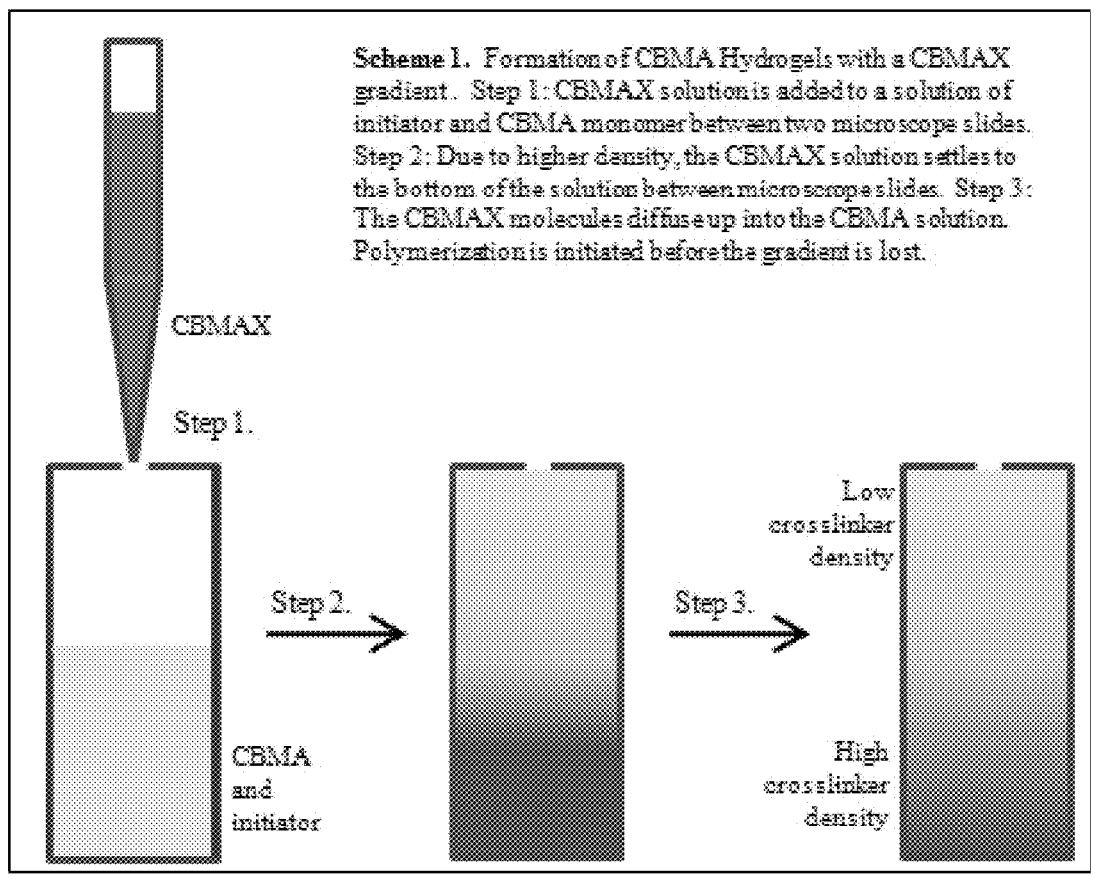
FIG. 10 is a schematic illustration of the preparation of a representative zwitterionic crosslinked hydrogel of the invention, CBMA/CBMAX, having a cros slinking gradient.
Figure 11:
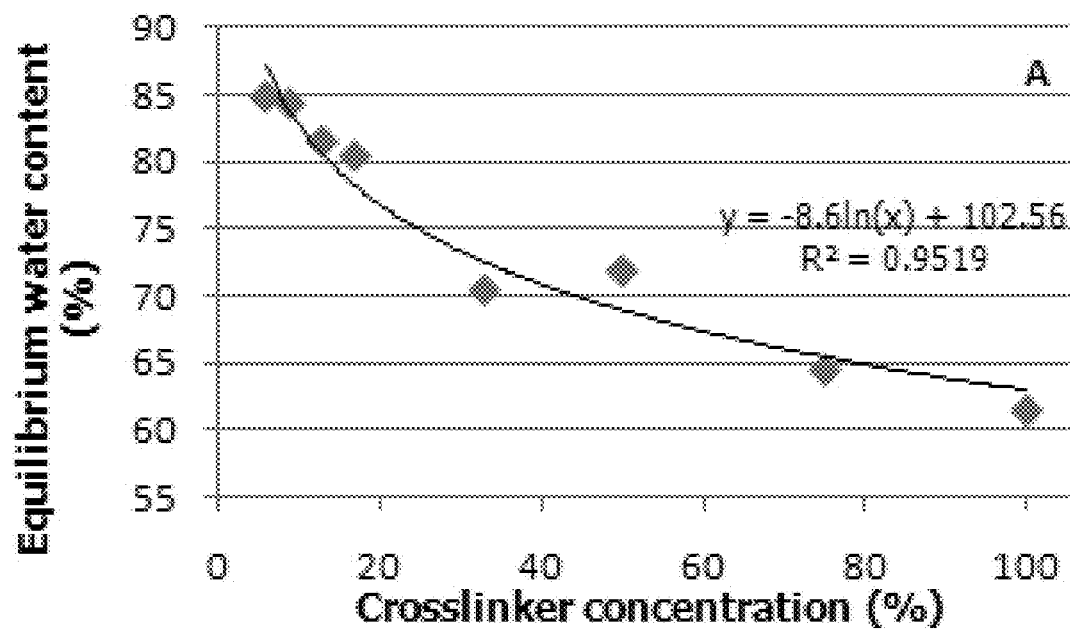
FIG. 11 compares the hydration properties (EWC) as a function of crosslinker concentration (%) of representative zwitterionic crosslinked polymers of the invention, CBMA/CBMAX, having a crosslinking gradient.
Figure 12:
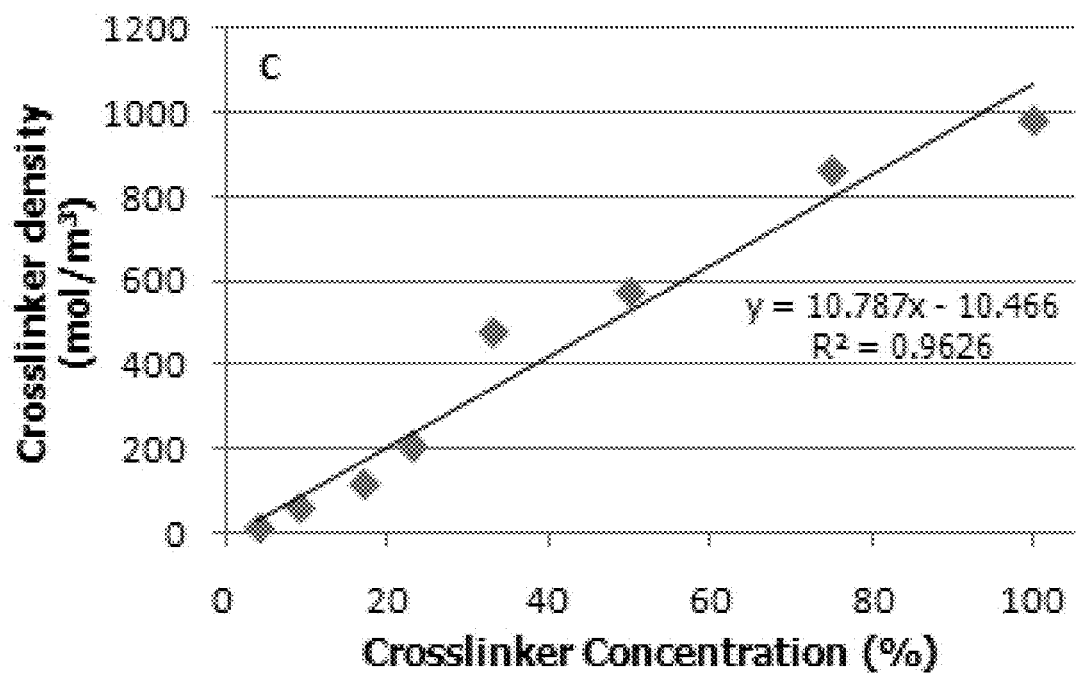
FIG. 12 compares the crosslinker density ($\mu mol/mm^3$) as a function of crosslinker concentration (%) of representative zwitterionic crosslinked polymers of the invention, CBMA/CBMAX, having a crosslinking gradient.
Figure 13:
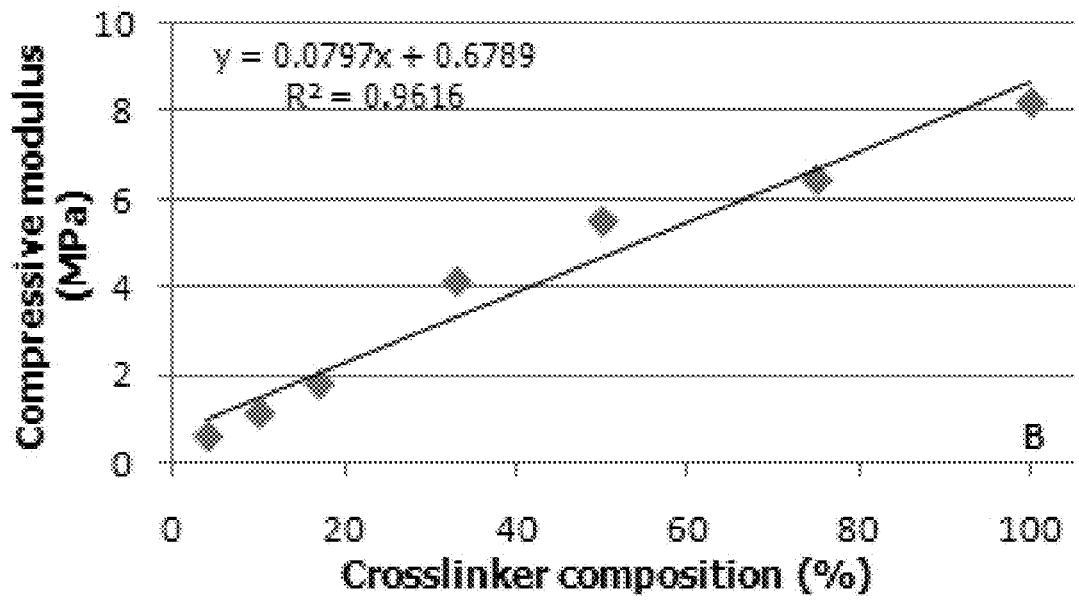
FIG. 13 compares the compressive modulus (MPa) as a function of crosslinker concentration (%) of representative zwitterionic crosslinked polymers of the invention, CBMA/CBMAX, having a crosslinking gradient.
Figure 14:
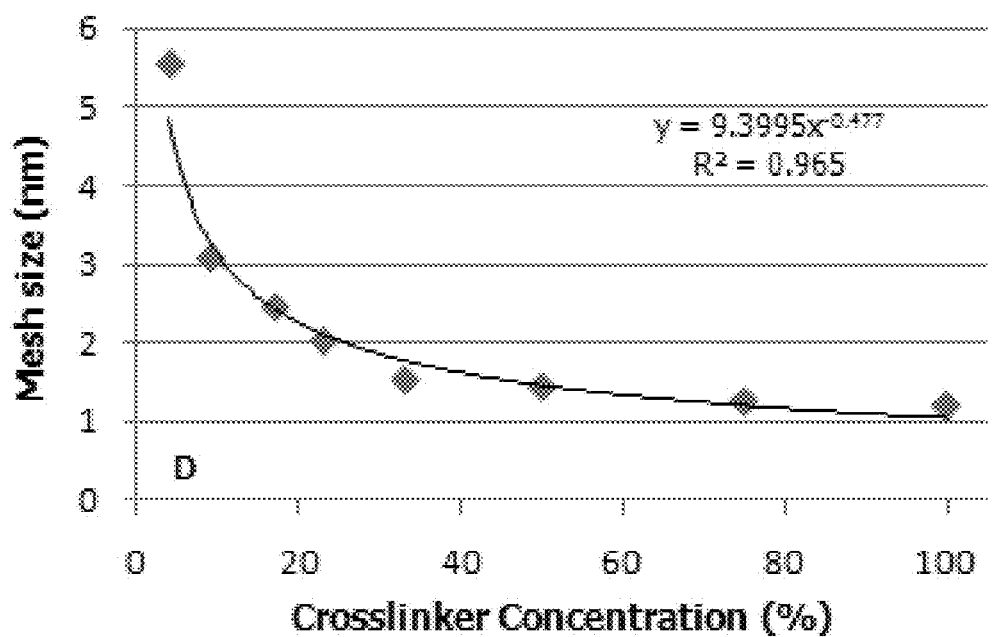
FIG. 14 compares the mesh size (nm) as a function of crosslinker concentration (%) of representative zwitterionic crosslinked polymers of the invention, CBMA/CBMAX, having a crosslinking gradient.

A monomer (CBMA) solution was prepared in 1M NaCl, at a concentration of 65% by weight. This solution was mixed with sonication and chilled. Photoinitiator, same as used above, was added to the monomer solution, and the monomer-initiator solution was loaded as-is between two microscope slides separated by a 2 mm-thick polytetrafluoroethylene (PTFE) spacer. Next, a 65%-by-weight solution of crosslinker (CBMAX) was prepared similarly, and also sonicated and chilled. This solution was carefully added to the monomer solution after the latter was loaded into the microscope slide apparatus. Due to different solution densities, the crosslinker solution appeared to settle to the bottom of the apparatus before diffusion created a crosslinker gradient. Visual observation of this phenomenon was made possible by trace amounts of colored material in the crosslinker. This process is illustrated in FIG. 10. Finally, but before diffusion homogenized the solution, polymerization was initiated by long wave UV light for 30 minutes, after which time the hydrogels was removed from the glass slides and hydrated in PBS for 5 days.

Gradient Analysis

The crosslinking profile of the gradient hydrogels was assayed by measuring the equilibrium water content along the length of the hydrogel slab. 5-mm disks were cut from contiguous sections along the edge of the gel, from the region of highest crosslinker concentration (more darkly colored, see FIG. 10) to the region of lowest crosslinker concentration. The disks were weighed, thoroughly dehydrated for 3 days at 50° C. and 30 in. Hg vacuum, and reweighed. The equilibrium water content of each disk was determined as EWC=100(%)*$(m_w-m_d)/m_w$, where $m_w$ is the mass of the wet hydrogel and an$_d$ is the mass of the dry hydrogel.

Hydrogel Characterization

Previously, equilibrium water content was measured for CBMA hydrogels with different CBMAX concentrations, ranging from 2% CBMAX to 100% CBMAX. Using this established relationship, it is possible to convert the equilibrium water content measured at different locations on the same CBMA/CBMAX hydrogel to CBMAX concentration at each particular location. Furthermore, using results from the extensive characterization of physical and mechanical properties performed in the preceding chapter, the crosslinker content profile can be correlated to its corresponding mechanical (compressive) modulus, mesh size, and crosslinking density (FIGS. 11-14).

Gradient Hydrogel Formation and Analysis

Figure 15:
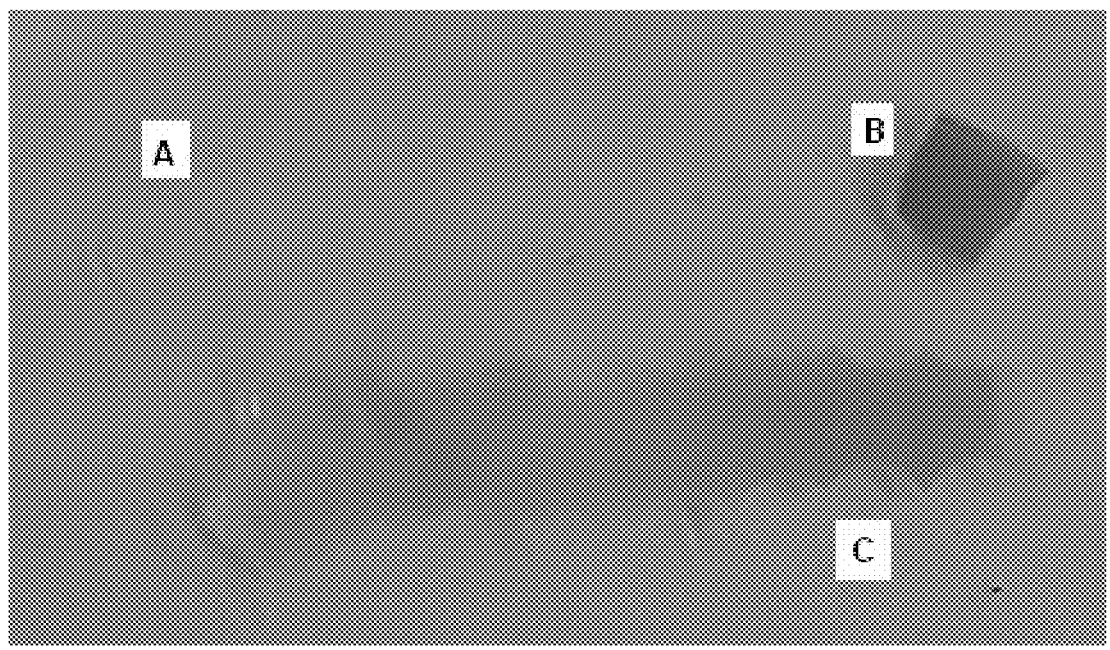
FIG. 15 is a photograph of representative CBMA/CBMAX gradient hydrogels: 5-mm diameter disk (A) of 4% CBMA-X CBMA hydrogel and a square of 75% CBMAX-hydrogel (B) are shown compared to the representative gradient hydrogel (C) to illustrate the gradient by color that accompanies CBMAX crosslinking.
Figure 16:
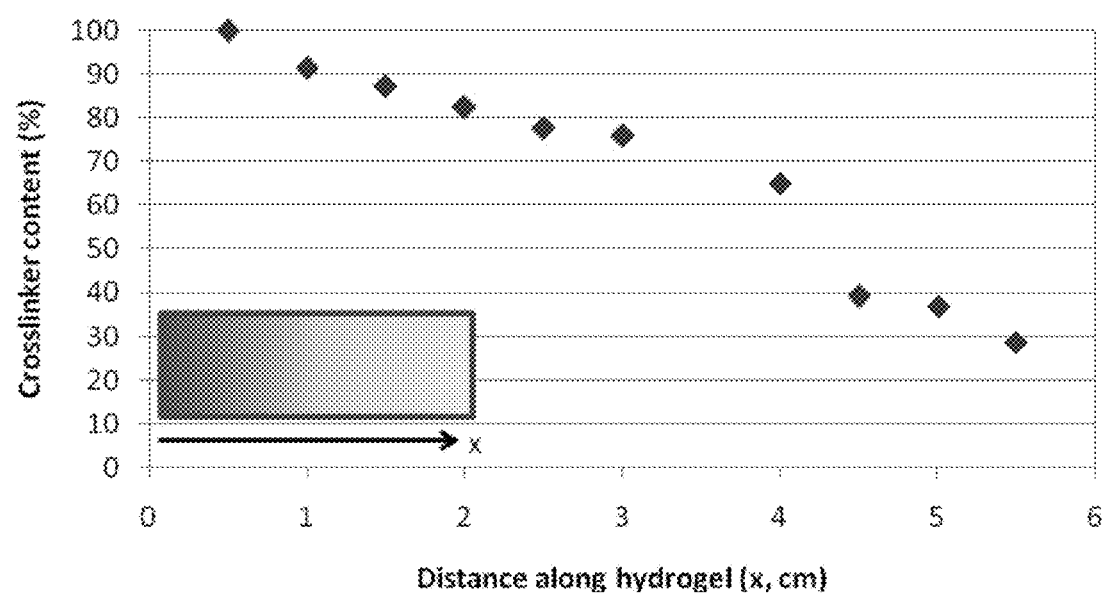
FIG. 16 is graph illustrating crosslinker content (%) as a function of distance (cm) along a representative gradient hydrogel.

The gradient gel was formed as described above. Due to a colored tracer included in the crosslinker, the gradient was visible to the naked eye (FIG. 15). The equilibrium water content was converted to crosslinker content using the relationship shown in FIG. 11. The crosslinker content as a function of distance along the gel starting at the highest crosslinker edge is shown in FIG. 16. The crosslinker content ranges from around 100% to 30%, with a fairly uniform gradient in the intermediate region, indicating successful formation of a single material with higher concentration of crosslinker at one end.

The hydrogel was made with diverse and spacially controlled properties. The crosslinker content ranges from around 100% to 30%, with a fairly uniform gradient in the intermediate region. Because the materials used, CBMA monomer and CBMA crosslinker, have identical backbone and side-chains, the overall hydrogel is composed essentially of a single material. Thus, the gradient in water content, crosslinker density, and mesh pore size did not compromise the continuity of certain desired properties, such as nonfouling and functionalizability.

The hydrogel is made from a single material and displays a uniform gradient of crosslinking and the corresponding physical, mechanical and hydration properties. The monomer and crosslinker differ from each other only by one or two methacrylate groups, and thus the entire structure is composed solely of zwitterionic carboxybetaine and methacrylate; the gradient is formed by a gradual increase in the methacrylate-to-zwitterionic ratio. Even at 100% crosslinker (2:1 methacrylate-to-zwitterionic), the hydrogel demonstrated 90% lower nonspecific cell adhesion than nonfouling pHEMA hydrogels and good functionalization. Thus, along the entire gradient, despite decreases in mechanical strength and crosslinker density and increases in pore size and hydration, the material remains zwitterionic and functionalizable, rendering the bioactivity of the gel controllable.

Example 5

Zwitterionic Poly(carboxybetaine) Hydrogels for Glucose Biosensor

In this example, the use of a representative zwitterionic crosslinked hydrogel of the invention, CBMA/CBMAX, in a glucose biosensor is described.

Preparation of polyCBMA Hydrogels.

CBMA monomer was first mixed with water and the solution was sonicated for 1 min to dissolve the monomer. CBMAX was added to the above solution and the mixture was sonicated for 1 min to complete dissolution at 0° C. The molar ratio of CBMA and CBMAX was 1000:1, 100:1, 10:1, and 5:1 and the final concentration of CBMA was 10 M. 1% (w/w) Photoinitiator (Benacure 1173) was added and the solutions mixed at 0° C. The solutions were transferred into a pair of glass plates, separated with a 0.4 mm PTFE spacer. The photo-polymerization reaction was carried out at room temperature for 30 min under a 365 nm UV light to polymerize the hydrogels. Then, the hydrogels were removed from the plates and immersed in a large volume of PBS. The PBS was changed daily for 5 days to remove residual chemicals before further use.

Analysis of mechanical and cell adhesion properties of hydrogels.

Figure 17:
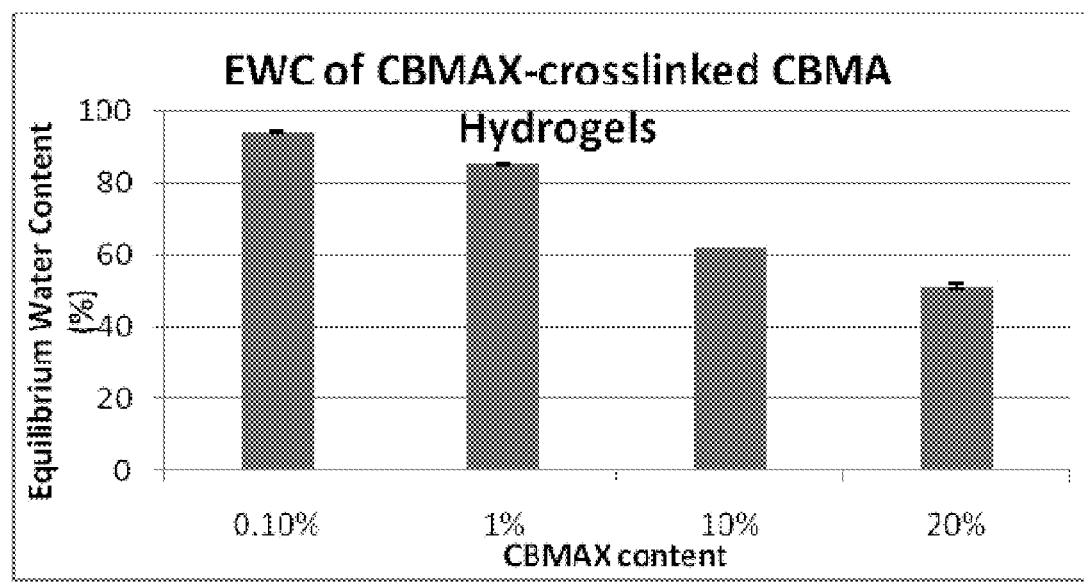
FIG. 17 compares water content (EWC) of representative CBMA/CBMAX hydrogels as a function of CBMAX content (0.1, 1, 10, and 20%).
Figure 18A:
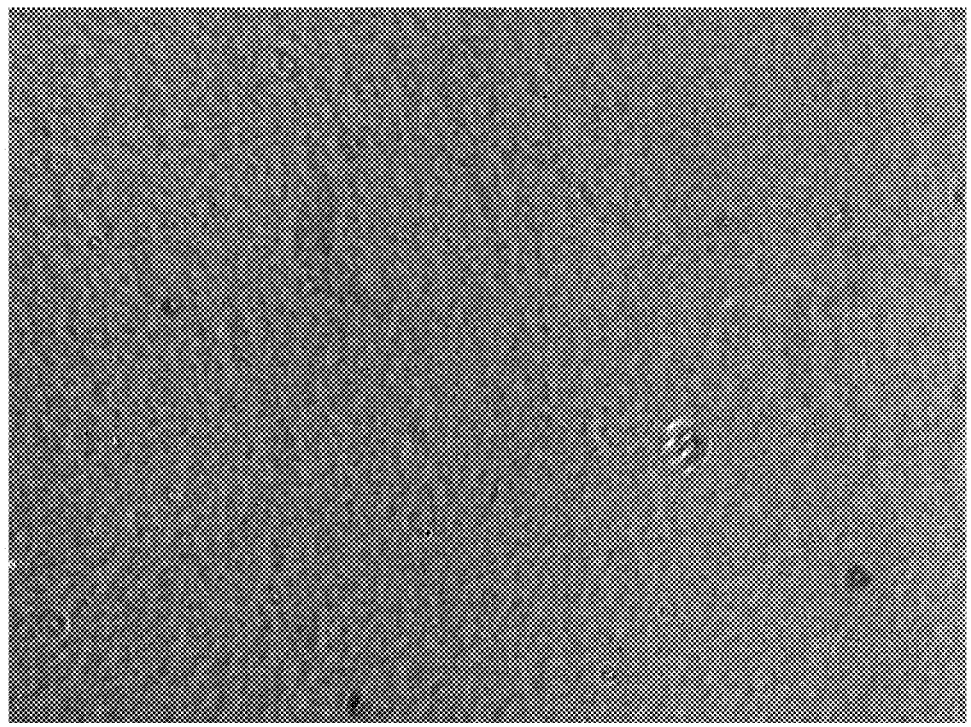
FIGS. 18A-18H are images comparing COS-7 cell attachment on representative CBMA/CBMAX hydrogels after a 3-day culture: hydrogel CBMAX content 0.1% before (FIG. 18A) and after GOx immobilization (FIG. 18B), 1% hydrogels before (FIG. 18C) and after GOx immobilization (FIG. 18D), 10% hydrogels before (FIG. 18E) and after GOx immobilization (FIG. 18F), and 20% hydrogels before (FIG. 18G) and after GOx immobilization (FIG. 18H).
Figure 18B:
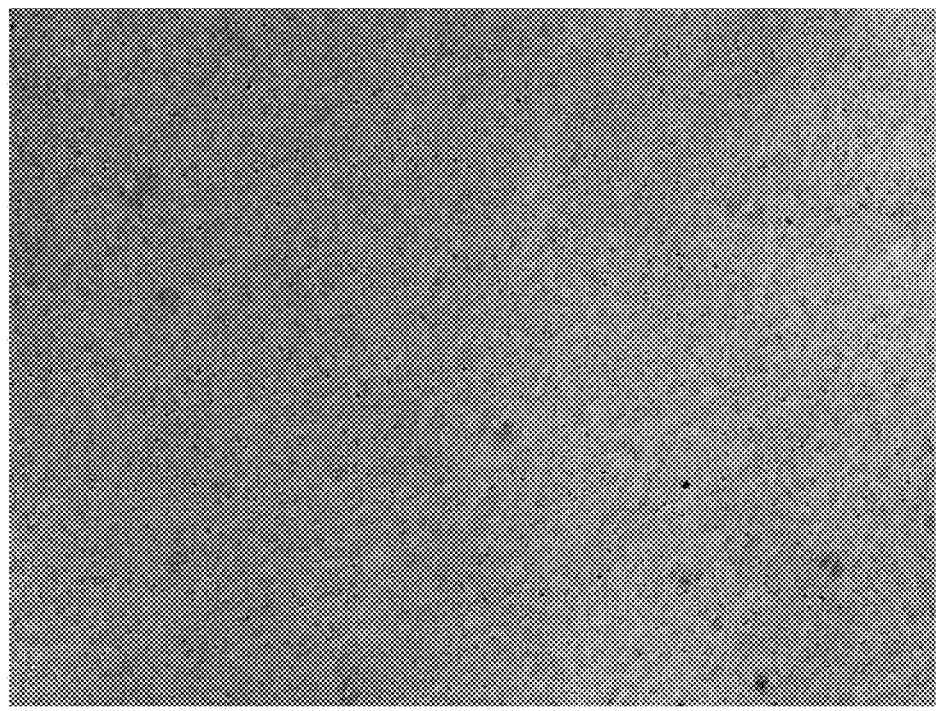
Figure 18C:
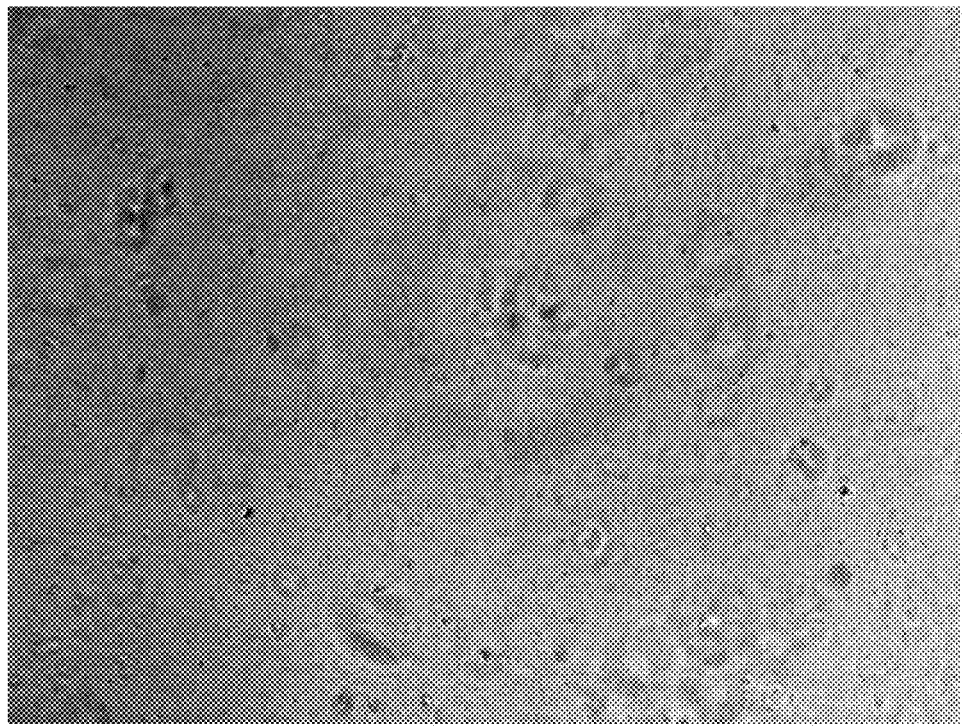
Figure 18D:
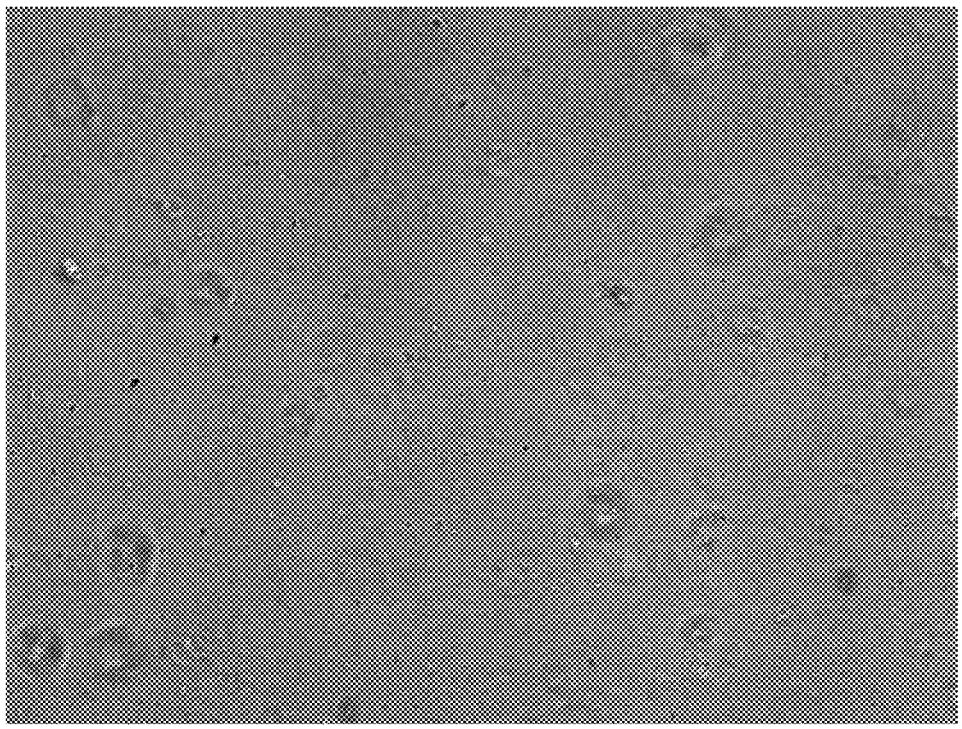
Figure 18E:
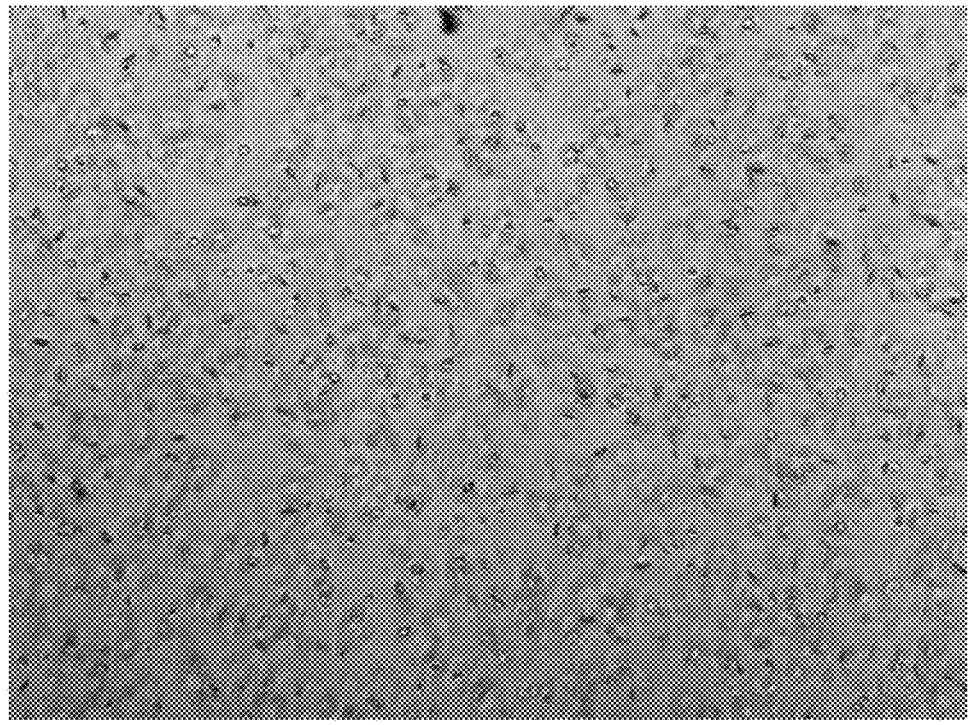
Figure 18F:
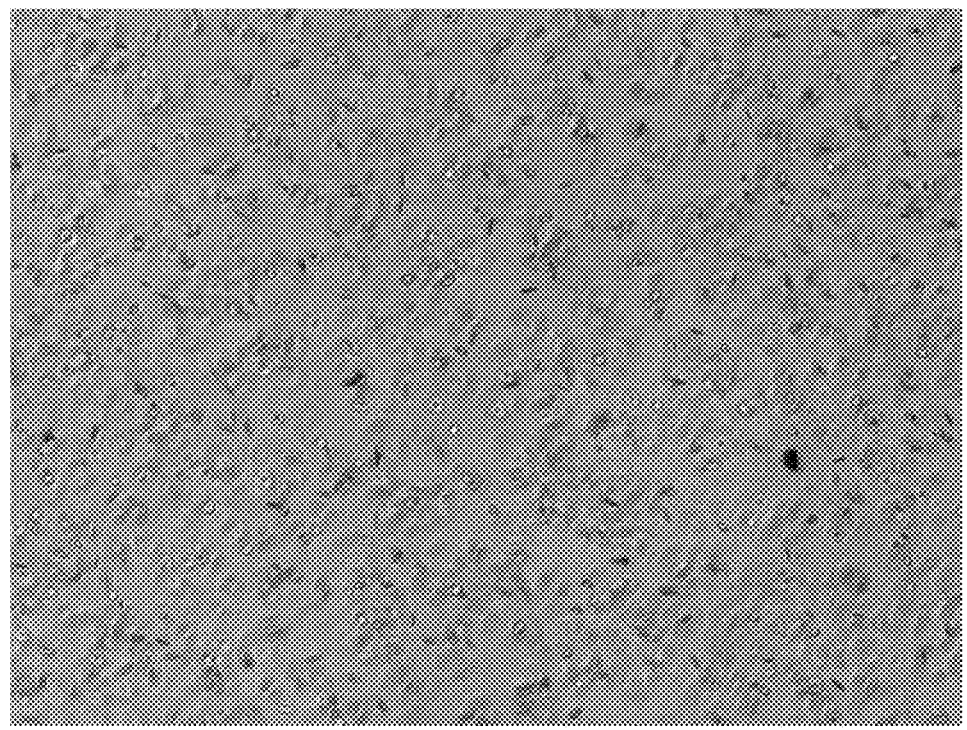
Figure 18G:
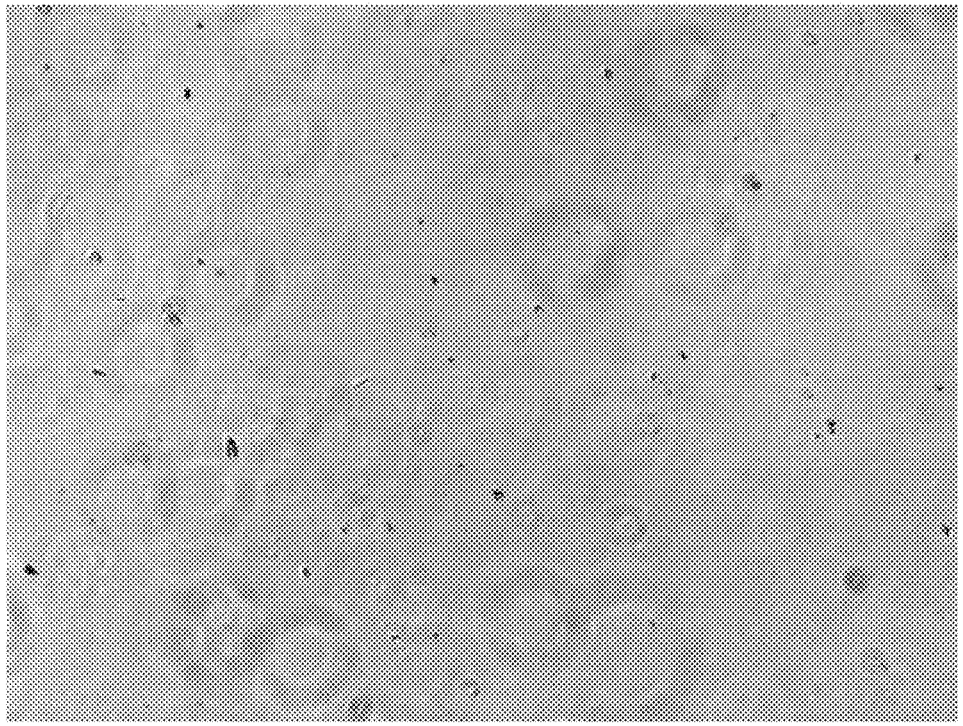
Figure 18H:
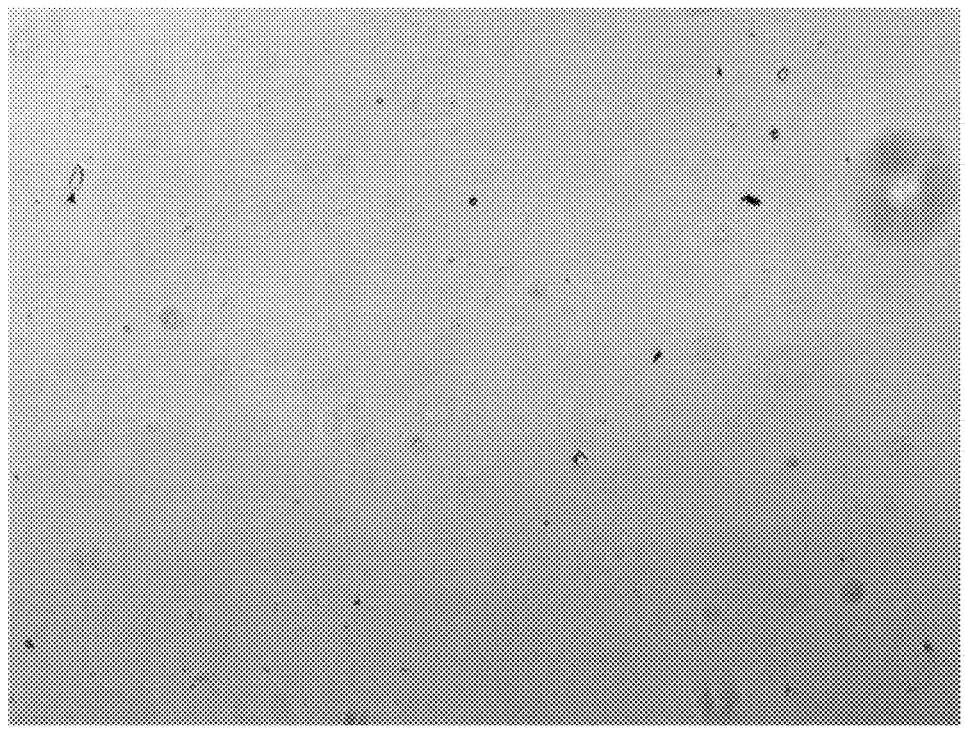
Figure 19A:
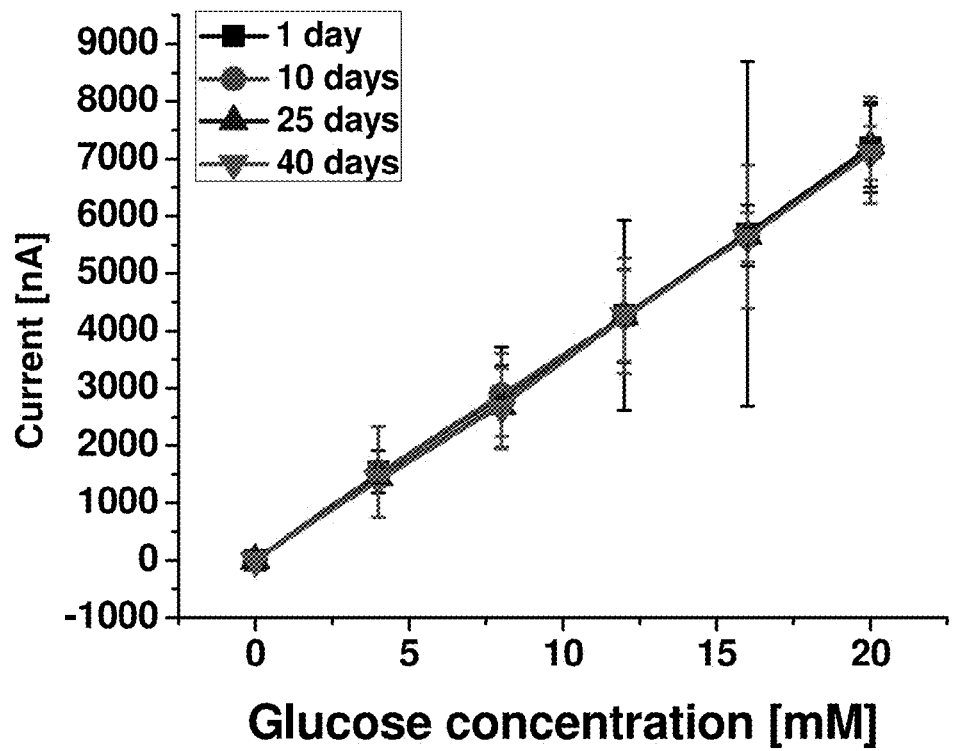
FIGS. 19A-19D compare current response (nA) of glucose sensors coated with representative CBMA/CBMAX hydrogels as a function of glucose concentration (mM) in PBS at 1, 10, 25, and 40 days: hydrogel CBMAX content 0.1% (FIG. 19A), 1% (FIG. 19B), 10% (FIG. 19C), and 20% (FIG. 19D). Operating potential: +0.75 V vs. Ag/AgCl reference electrode.
Figure 19B:
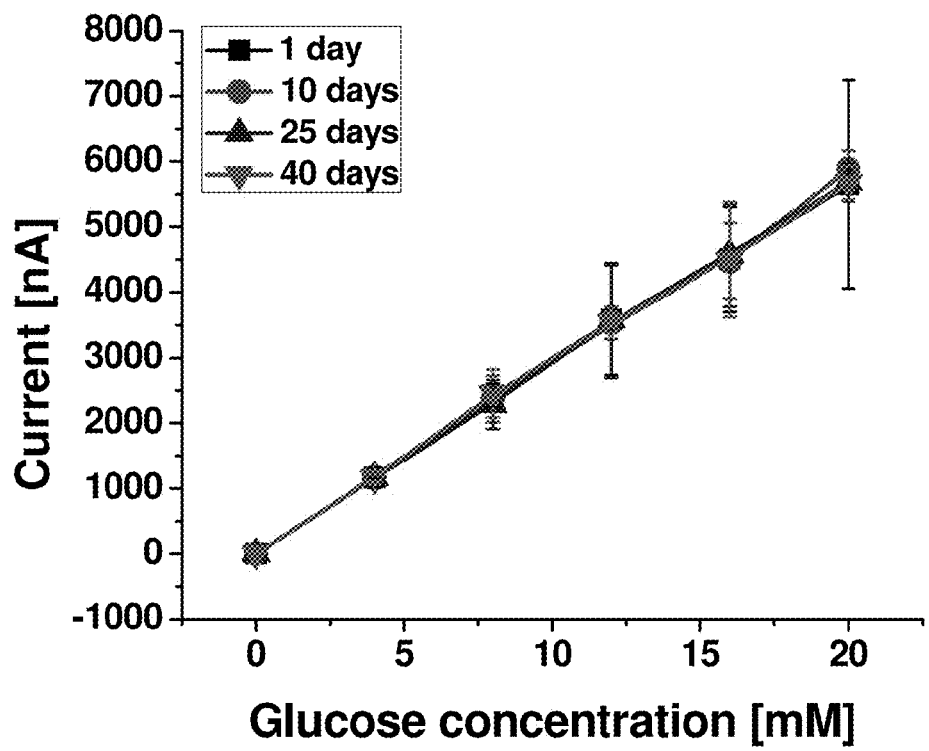
Figure 19C:
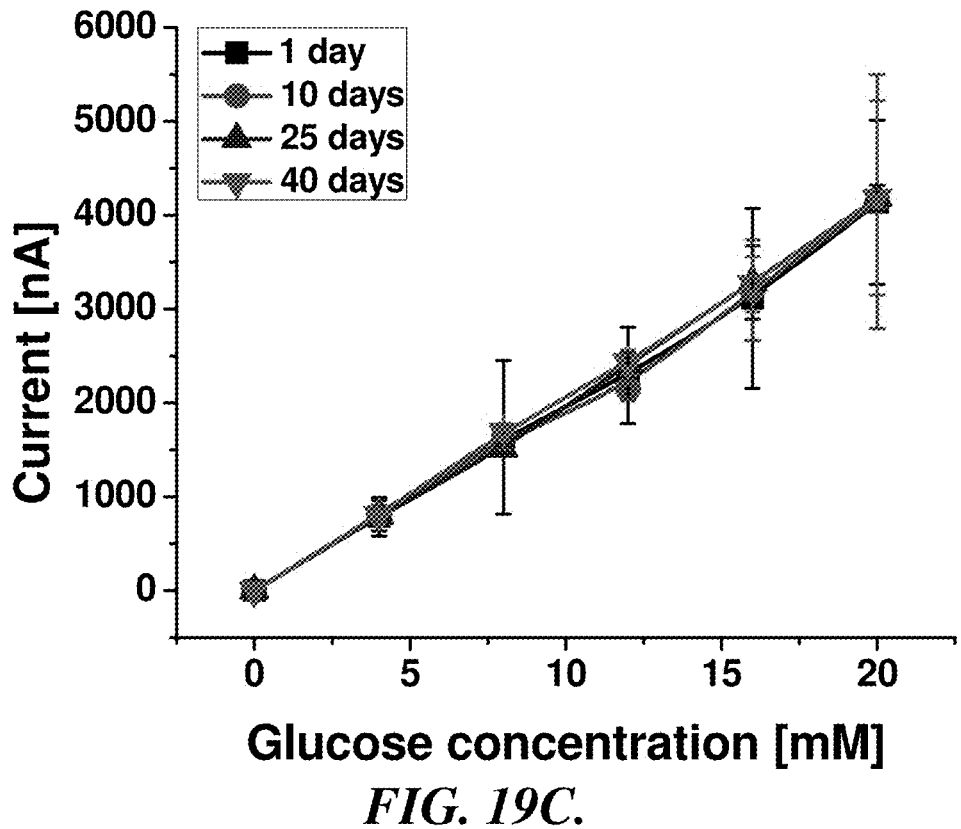
Figure 19D:
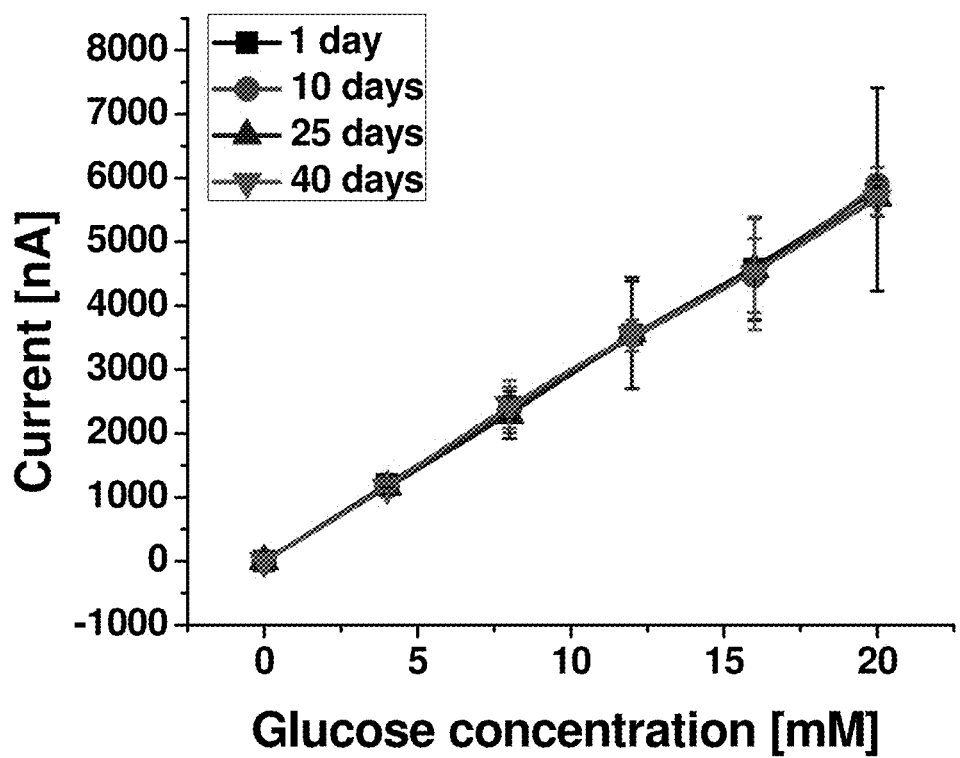
Figure 20A:
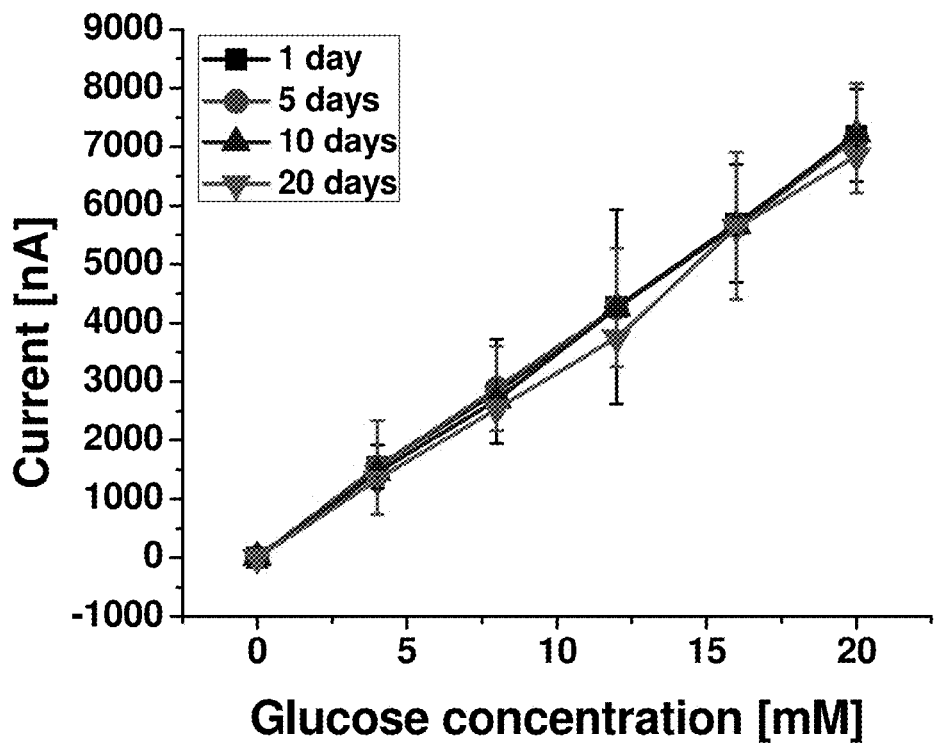
FIGS. 20A-20D compare current response (nA) of glucose sensors coated with representative CBMA/CBMAX hydrogels as a function of glucose concentration (mM) in 100% blood serum at 1, 10, 25, and 40 days: hydrogel CBMAX content 0.1% (FIG. 20A), 1% (FIG. 20B), 10% (FIG. 20C), and 20% (FIG. 20D). Operating potential: +0.75 V vs. Ag/AgCl reference electrode.
Figure 20B:
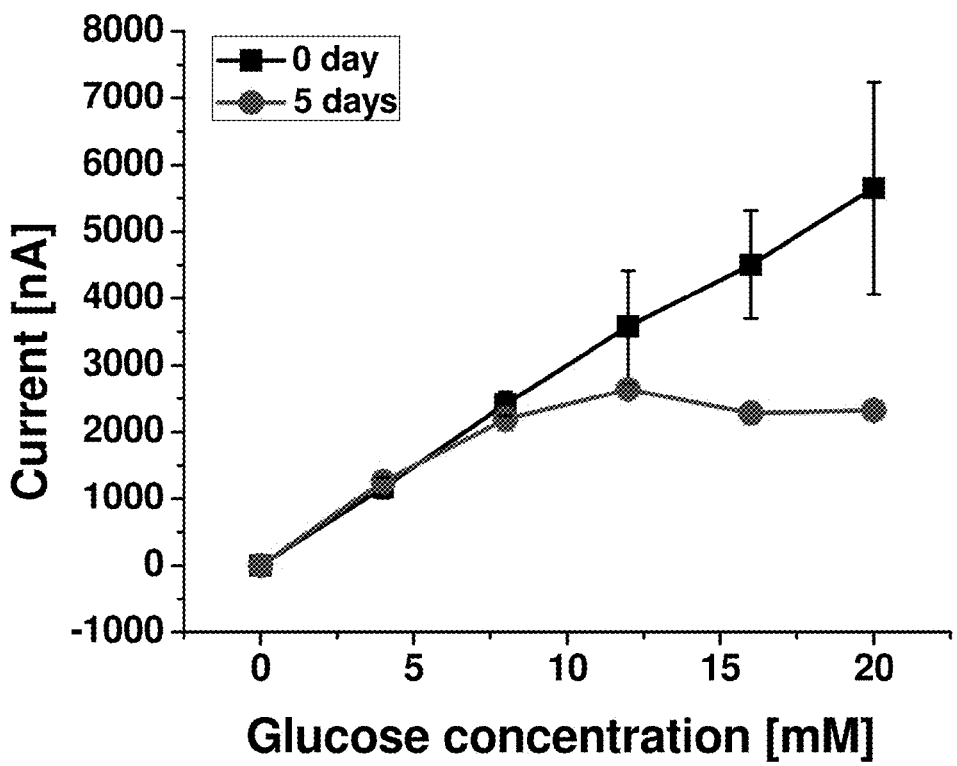
Figure 20C:
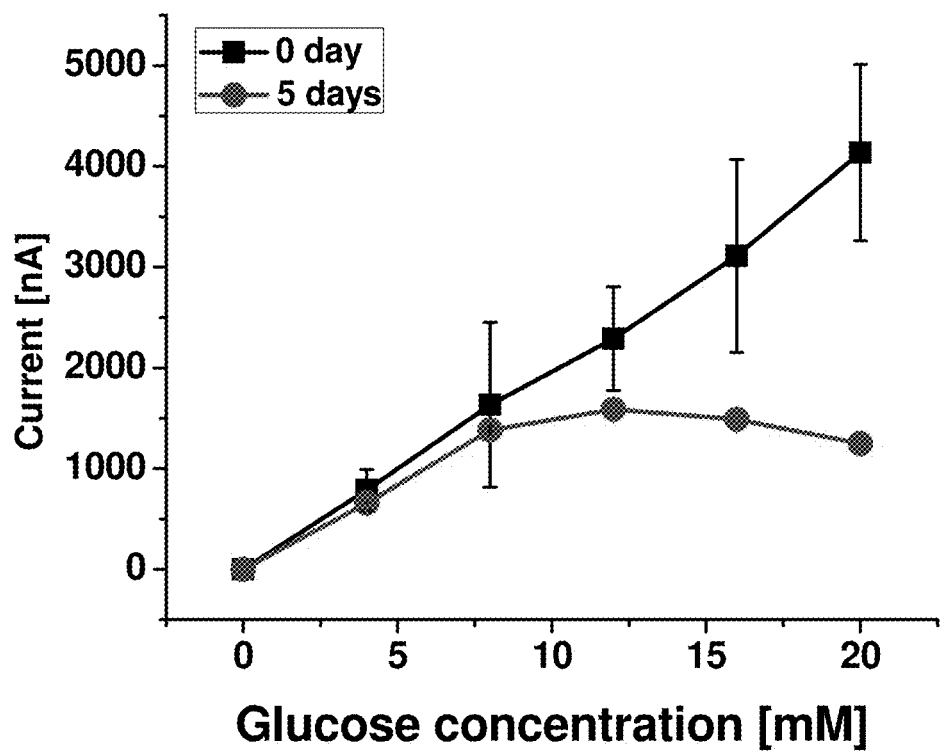
Figure 20D:
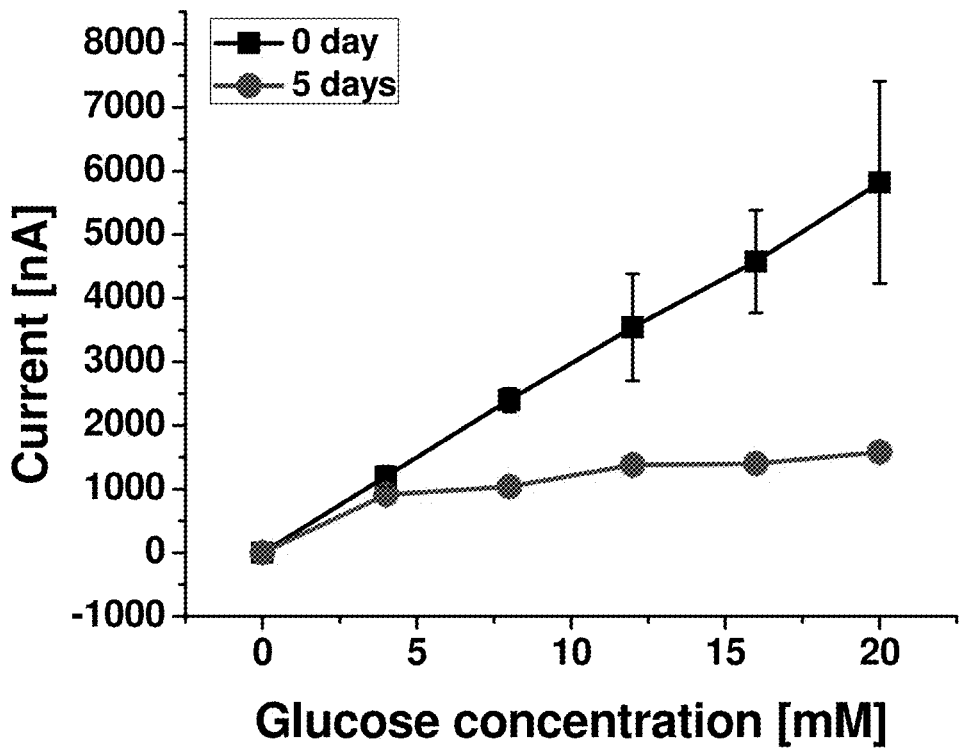

Hydrogels were allowed to swell to equilibrium in PBS buffer for five days. The equilibrated hydrogels were then punched into disks with a diameter of 5 mm. The disks were weighed and then dehydrated under vacuum at 50° C. and 30 in. Hg vacuum for 3 days. The swelling ratios were determined by the ratio of the swollen hydrogels weight to the dry hydrogels weight and the equilibrium water content values were determined as described above. All samples were measured in triplicate. As shown in FIG. 17, the highest water content was obtained for 0.1% CBMAX hydrogels, which was 94.19±0.26%. With the increase of the CBMAX molar ratio, the water content decreased.

Three hydrogel disks of 5 mm diameter (0.5 mm thickness when cast) were placed individually in the wells of a 48-well plate with 500 μL PBS solution. To sterilize the hydrogels, they were refrigerated overnight in 1× penicillin-streptomycin in PBS. COS-7 cells (p='7) were seeded onto the hydrogels at a concentration of $1 \times 10^4$ cells/mL in supplemented DMEM. Cells were allowed to grow for 72 hours at 37° C., 5% $CO_2$, and 100% humidity, after which time the hydrogels were photographed at 10× magnification with a Nikon Eclipse TE2000-U microscope. Photographs were taken at five predetermined areas on the surface of the hydrogels, for a total of fifteen images per hydrogel formulation. The difference in cell binding on the surface of different CBMAX molar ratio polyCBMA hydrogels before and after GOx immobilization is shown quantitatively in FIGS. 18A-18H. All the polyCBMA hydrogels except 10% CBMAX molar ratio hydrogels were highly resistant to cell attachment before and after GOx immobilization; there was an extremely low amount of cell adhesion to the surface.

Preparation of polyCBMA hydrogel-coated glucose sensors.

Glucose sensors were based on the coil-type implantable sensor. The coil-type glucose biosensors were prepared by winding the top 10 mm of a 40-50 mm long platinum wire along a 25-gauge needle to form a coil-like cylinder. To improve the adhesion of the polyCBMA hydrogels, the surface of the coils was functionalized using a solution of 10% (trimethoxysilyl)propyl methacrylate and 0.5% water in toluene at 80° C. For formation of the hydrogel coating on the glucose sensor tip, 1.2 μL of the mixed solution (CBMA, CBMAX, and photoinitiator along with water) was pipetted onto the sensor tip. The solution was allowed to spread evenly over the surface of the tip. After exposing to 254 nm UV light for 30 min, the sensors (referred to as Pt/CBMA/GOx) were stored in PBS until further use.

Enzyme immobilization via NHS/EDC chemistry.

The carboxylate groups of the polyCBAA hydrogel were activated by injection of a freshly prepared solution of N-hydroxysulfosuccinimide sodium (5 mM) and N-ethyl-N'-(3-diethylaminopropyl) carbodiimide hydrochloride (EDC) (100 mM) in 10 mM MES buffer (pH 5.5, 100 mM NaCl) for 2 h at 25° C. Then, the sensors were removed and immersed in a large volume of the above MES buffer for 2 h. The MES buffer was changed several times to remove residual chemicals. The sensors were immersed in a freshly prepared solution of glucose oxidase (GOx) (10 mg/mL) in MES buffer for 4 h at 4° C. followed with a freshly prepared solution of glucose oxidase (GOx) (1 mg/mL) in PBS buffer for 2 h at 4° C. Before further glucose test, the sensors were immersed in a large volume of PBS to remove all unsteady binding.

Sensor Evaluation In Vitro.

The in vitro performance of the sensors was examined in glucose PBS solution to determine sensitivity and linear range of sensors. The sensitivity of the Pt/CBMA/GOx sensors was first measured using 4 and 20 mM glucose PBS solution. The difference between the base current of PBS and the steady state current of glucose in the sample was used to obtain the calibration graph. Then, the sensors were examined with glucose solution dispersed in 100% human blood serum. For the long-term sensor evaluation, the sensors were dipped into 100% human blood serum at 4° C. before the next test at different incubating days. When determining glucose in a serum sample, the base current was taken in the serum and then the sensor was transferred into the sample to obtain a steady state current. All experiments were carried out at room temperature and all the solution was stirred during the measurement. Amperometric measurements were performed at room temperature at +0.75 V vs. Ag/AgCl and a platinum wire counter electrode. The current responses of glucose sensors coated with different CBMAX molar ratio polyCBMA hydrogels as a function of glucose concentration in PBS are compared in FIGS. 19A-19D. All the sensors display very high sensitivity and current response to glucose in PBS. Furthermore, their response did not delay with excellent linearity over the 4-20 mM range. The current responses of glucose sensors coated with different CBMAX molar ratio polyCBMA hydrogels as a function of glucose concentration in 100% blood serum are compared in FIGS. 20A-20D. The sensors coated with 0.1% CBMAX molar ratio polyCBMA hydrogels did not show a decline in either sensitivity or linearity after exposure to blood samples over 10 days while the other sensors failed to perform well. The result suggests that the addition of polyCBMA hydrogel coating improves the long-term performance of the implanted glucose sensors.

Example 6

Zwitterionic Poly(carboxybetaine) Hydrogels for Gold Nanoparticles

In this example, the use of a representative zwitterionic crosslinked hydrogel of the invention, CBMA/CBMAX, in a glucose biosensor is described.

Synthesis of Initiator-Modified Gold Nanoparticles (GNPs).

5 mM aqueous solution of either $HAuCl_4$ (30 mL) was added to a 4 mM solution of tetraoctylammonium bromide (TOAB) in toluene (80 mL) under stirring for 10 min. Aqueous solution $NaBH_4$ (0.4 M, 25 mL) was then added dropwise to this solution while vigorously stirring. The dark orange solution turned red within a minute, and the stirring was continued for 3 h to make sure the reaction was complete. Then the two phases were separated, and the organic phase was subsequently washed with 0.1 M $H_2SO_4$, 0.1 M NaOH, and water (three times each). Then, initiator, 274.2 mg of 11-mercaptoundecyl 2-bromoisobutyrate (Br$(CH_3)_2$COO$(CH_2)_{11}$SH) (0.808 mmol, dissolved in 1 mL toluene) were added to the solution in a dropwise fashion within 15 min. The reaction was allowed to proceed for overnight. Methanol (60 mL) was added to the system to precipitate the Au-NPs. The precipitate was collected and re-dispersed in toluene and precipitated again into ethanol. This precipitation and re-dispersion cycle was repeated twice before the pure Au-NPs (i.e. free of reaction byproducts) were obtained. The NPs were well dispersed in acetone without aggregation and the average diameter of the Au-NPs was about 5 nm.

Preparation of CBMA coated GNPs via ATRP (CA-GNPs).

300 mg CBMA monomer, 61.70 mg 2,2-bipyridine, and 28.53 mg copper(I) bromide were dissolved in 3 ml degassed acetone and 0.5 ml methanol under nitrogen atmosphere. 1 mL initiator-modified GNPs solution was deoxygenated by bubbling nitrogen before mixed with above solution. The final mixture was stirred (100 rpm) at room temperature for 2 h. After the polymerization, CA-GNPs were washed several times by centrifuging/redispersing in water. The average diameter of the CA-NPs was 69.8 nm in water.

Preparation of OEGMA coated GNPs via ATRP (OA-GNPs).

47.7 mg copper(I) bromide, 7.43 mg copper(II) bromide, and 104 mg 2,2-bipyridine were dissolved in 4 ml degassed acetone under nitrogen. 1 mL initiator-modified GNPs solution was deoxygenated by bubbling nitrogen before directly mixed with the above solution. 2 g macromonomer OEGMA was added and the final mixture was stirred at room temperature for 6 h. After the polymerization, OA-GNPs were washed several times by centrifuging/redispersing in Milli-Q water. The average diameter of the OA-NPs was 72.4 nm in water.

Preparation of OEGMA coated GNPs via ATRP with addition of EGDMA crosslinker (OC-GNPs).

47.7 mg copper(I) bromide, 7.43 mg copper(II) bromide, and 104 mg 2,2-bipyridine were dissolved in 4 ml degassed acetone under nitrogen. 1 mL initiator-modified GNPs solution was deoxygenated by bubbling nitrogen before directly mixed with the above solution. 2 g macromonomer OEGMA and 126.4 μL EGDMA was added and the final mixture was stirred at 50° C. for 6 h. After the polymerization, OC-GNPs were washed several times by centrifuging/redispersing in Milli-Q water. The average diameter of the OC-NPs was 71.9 nm in water.

Preparation of CBMA coated GNPs via ATRP with addition of CBMAX crosslinker (CC-GNPs).

300 mg CBMA monomer, 3.0 mg CBMAX, 61.7 mg 2,2-bipyridine, 4.4 mg copper(II) bromide and 28.533 mg copper(I) bromide were dissolved in 3 ml degassed acetone and 0.5 ml methanol under nitrogen atmosphere. 1 mL initiator-modified GNPs solution was deoxygenated by bubbling nitrogen before directly mixed with the above solution. The final mixture was stirred at 50° C. for 6 h. After the polymerization, CCE-GNPs were washed several times by centrifuging/redispersing in Milli-Q water. The average diameter of the CC-NPs was 80 nm in water.

Stability test of polymer-coated GNPs.

Figure 21:
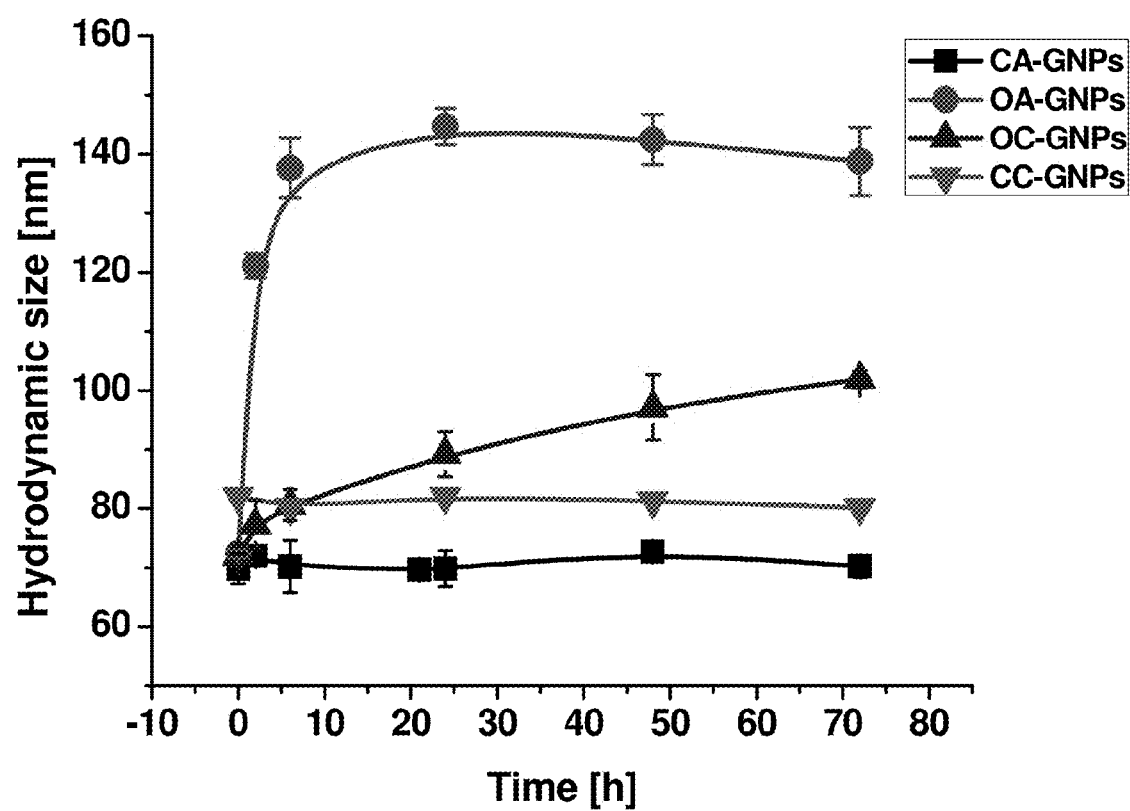
FIG. 21 compares hydrodynamic size of OA-GNPs, OC-GNPs, CA-GNPs, and CC-GNPs in undiluted blood serum. Serum proteins are removed by centrifuge and redispersed in PBS before measurement.

The stability of polymer-coated GNPs was further evaluated in 100% human blood serum at 37° C. Due to high protein concentrations, these nanoparticles were separated from human blood serum proteins by centrifugation and re-dispersed in PBS buffer. The average diameter of the nanoparticles was then evaluated by DLS at 37° C. All the solutions were mixed with 100% human blood serum at 37° C. before the next test at different incubating time. As shown in FIG. 21, OA-GNPs showed a size increase of about 50 nm in a very short period of time. At the end of 72 h, the diameter increased to about 140 nm, indicating significant protein adsorption and particulate aggregation. Although OC-GNPs were not stable in such extreme situation, the addition of EGDMA helped to enhance the stability. The diameter increments were 6 nm and 30 nm after an incubation period of 6 h and 72 h, respectively. Precipitates could be observed in the above solutions. However, three kinds of GNPs with the protection of polyCBAA coating (CA-GNPs, CCE-GNPs, and CCC-GNPs), the interactions between proteins and nanoparticles did not cause any agglomeration and the particle sizes after their separation from human blood serum proteins was almost the same as those without serum (70 nm, 50 nm and 105.9 nm), indicating their excellent stability.

Figure 22:
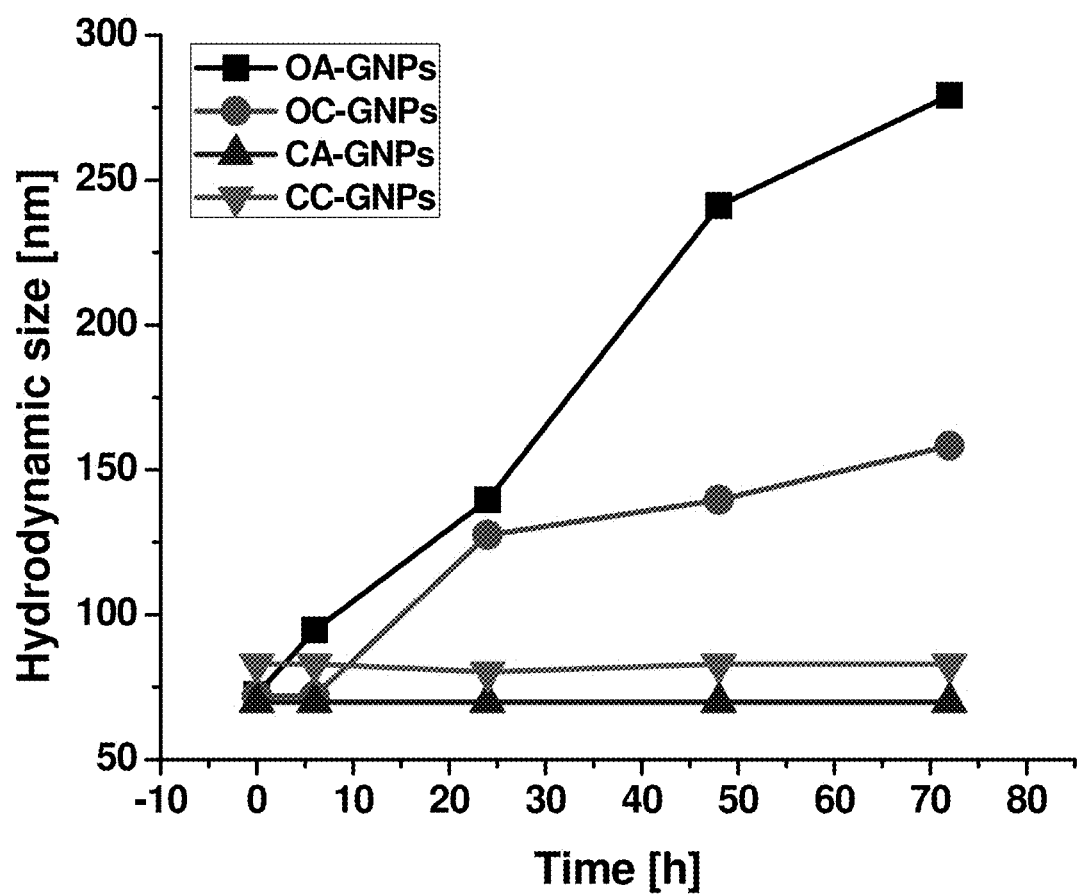
FIG. 22 compares hydronamic size of OA-GNPs, OC-GNPs, CA-GNPs, and CC-GNPs mixed with undiluted blood serum.

Next, polymer-coated nanoparticles were mixed with human blood serum at a very high concentration and incubated at 37° C. The average diameter of the nanoparticles was then evaluated by DLS at 37° C. As shown in FIG. 22, the OA-GNPs showed an increase of about 20 nm in size after 6 h. This value increased to 200 nm after 72 h, which was attributed to the interactions of nanoparticles with proteins in the incubation serum medium. Again, the addition of EGDMA increased the stability. The diameter increment was 70 nm after an incubation period of 72 h. However, with polyCBMA coating, there is no agglomeration and all three samples showed good stability without obvious size increase during the test period of 72 h.

While illustrative embodiments have been illustrated and described, it will be appreciated that various changes can be made therein without departing from the spirit and scope of the invention.

The invention claimed is:

1. A crosslinked hydrogel, comprising:
a crosslinked polymer having repeating units comprising a plurality of positively charged repeating units and a plurality of negatively charged repeating units, wherein the crosslinked ratio of the number of positively charged repeating units to the number of the negatively charged repeating units is from about 1:1.1 to about 1:0.5; and
a plurality of crosslinks,
wherein each crosslink is represented by the formula:

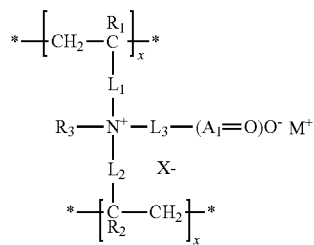

wherein
$R_1$ and $R_2$ are independently selected from the group consisting of hydrogen, fluorine, trifluoromethyl, C1-C6 alkyl, and C6-C12 aryl groups;
$R_3$ is selected from the group consisting of C1-C6 alkyl, C6-C12 aryl, $CH_2$=$C(R_1)$-$L_1$-, $CH_2$=$C(R_2)$-$L_2$-, or $R_3$ is the residual portion of a third crosslink, -$L_1$-$CR_1$—$CH_2$— or -$L_2$-$CR_2$—$CH_2$—;
$L_1$ and $L_2$ are independently selected from the group consisting of —C(=O)O—$(CH_2)_n$— and —C(=O)NH—$(CH_2)_n$—, wherein n is an integer from 1 to 20;
$L_3$ is —$(CH_2)_n$—, where n is an integer from 1 to 20;
$A_1$ is C, S, SO, or PO;
x is an integer from about 5 to about 10,000;
$X^-$ is a counter ion associated with the $N^+$ cationic center; and
$M^+$ is a counter ion associated with the (A=O)$O^-$ anionic center.

2. The crosslinked hydrogel of claim 1, wherein each repeating unit is represented by the formula:

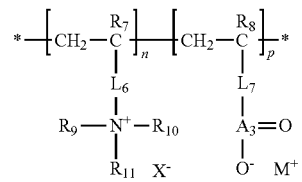

wherein
$R_7$ and $R_8$ are independently selected from hydrogen, fluorine, trifluoromethyl, C1-C6 alkyl, and C6-C12 aryl groups;
$R_9$, $R_{10}$, and $R_{11}$ are independently selected from alkyl and aryl, or taken together with the nitrogen to which they are attached form a cationic center;
$A_3$(=O)—OM) is an anionic center, wherein $A_3$ is C, S, SO, or PO, and M is a metal or organic counterion;
$L_6$ is a linker that covalently couples the cationic center [$N^+(R_9)(R_{10})(R_{11})$] to the polymer backbone;
$L_7$ is a linker that covalently couples the anionic center [$A_3$(=O)—OM] to the polymer backbone;
$X^-$ is the counter ion associated with the cationic center [N+(R9)(R10)(R11)];
$M^+$ is a counter ion associated with the (A=O)$O^-$ anionic center;
n is an integer from 5 to about 10,000; and
p is an integer from 5 to about 10,000.

3. The hydrogel of claim 2, wherein $R_1$, $R_2$, $R_3$, $R_7$, $R_8$, $R_9$, $R_{10}$, and $R_{11}$ are independently selected from the group consisting of C1-C3 alkyl.

4. The hydrogel of claim 2, wherein $R_7$, $R_8$, $R_9$, $R_{10}$, and $R_{11}$ are methyl.

5. The hydrogel of claim 1, wherein $L_1$ and $L_2$ are —C(=O)O—$(CH_2)_n$—, wherein n is 1-6.

6. The hydrogel of claim 1, wherein $L_3$ is —$(CH_2)_n$—, where n is an integer from 1-6.

7. The hydrogel of claim 2, wherein $L_6$ is selected from the group consisting of —C(=O)O—$(CH_2)_n$— and —C(=O)NH—$(CH_2)_n$—, wherein n is an integer from 1-20.

8. The hydrogel of claim 2, wherein $L_7$ is a C1-C20 alkylene chain.

9. The hydrogel of claim 2, wherein $L_6$ and $L_7$ are —C(=O)O—$(CH_2)_2$—.

10. The hydrogel of claim 1, wherein $A_1$ is C or SO.

11. The hydrogel of claim 2, wherein $M^+$ at each occurrence is selected from the group consisting of a metal and organic ion.

12. The hydrogel of claim 2, wherein $X^-$ at each occurrence is selected from the group consisting of halide, carboxylate, alkylsulfonate, sulfate, nitrate, perchlorate, tetrafluoroborate, hexafluorophosphate, trifluoromethylsulfonate, bis(trifluoromethylsulfonyl)amide, lactate, and salicylate.

13. The hydrogel of claim 1, wherein x is an integer from about 10 to about 1,000.

14. The hydrogel of claim 2, wherein n is an integer from about 10 to about 1,000.

15. The hydrogel of claim 2, wherein p is an integer from about 10 to about 1,000.

16. The hydrogel of claim 1, wherein the hydrogel is a gradient hydrogel.

17. The hydrogel of claim 1, further comprising a particle encapsulated therein.

18. The hydrogel of claim 17, wherein the particle is a nanoparticle.

19. The hydrogel of claim 18, wherein the nanoparticle has a diameter of about 5 nm to about 200 nm.

20. The hydrogel of claim 18, wherein the nanoparticle is a gold nanoparticle.

21. The hydrogel of claim 18, wherein the nanoparticle is a polymer-coated nanoparticle.

22. The hydrogel of claim 21, wherein the nanoparticle is coated with a polymer comprising carboxybetaine methacrylate (CBMA) or oligo(ethylene glycol) methyl ether methacrylate (OEGMA).

23. A surface of a substrate, wherein the surface comprises a hydrogel of claim 1.

24. The surface of claim 23, wherein the substrate is selected from the group consisting of a medical device, a glucose sensor, a particle, a drug carrier, a non-viral gene delivery system, a biosensor, a membrane, an implantable sensor, a subcutaneous sensor, an implant, and a contact lens.

25. The surface of claim 24, wherein the particle is a nanoparticle.

* * * * *